US009125552B2

(12) United States Patent
Dunki-Jacobs et al.

(10) Patent No.: US 9,125,552 B2
(45) Date of Patent: Sep. 8, 2015

(54) OPTICAL SCANNING MODULE AND MEANS FOR ATTACHING THE MODULE TO MEDICAL INSTRUMENTS FOR INTRODUCING THE MODULE INTO THE ANATOMY

(75) Inventors: Robert J. Dunki-Jacobs, Mason, OH (US); Randal T. Byrum, South Lebanon, OH (US); Jane A. Sheetz, Cincinnati, OH (US); Sean P. Conlon, Loveland, OH (US); David C. Youmans, Loveland, OH (US); Robert M. Trusty, Cincinnati, OH (US); Kurt R. Bally, Lebanon, OH (US); Gary L. Long, Cincinnati, OH (US); Paul G. Ritchie, Loveland, OH (US); Michael S. Cropper, Edgewood, KY (US); Thomas W. Huitema, Cincinnati, OH (US); Bradley E. White, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1485 days.

(21) Appl. No.: 11/830,953

(22) Filed: Jul. 31, 2007

(65) Prior Publication Data
US 2009/0036734 A1    Feb. 5, 2009

(51) Int. Cl.
*A61B 1/00* (2006.01)
*A61B 17/064* (2006.01)
(Continued)

(52) U.S. Cl.
CPC ......... *A61B 1/00096* (2013.01); *A61B 1/00172* (2013.01); *A61B 1/00183* (2013.01); *A61B 1/041* (2013.01); *A61B 5/0062* (2013.01);
(Continued)

(58) Field of Classification Search
USPC .............. 188/71.1; 227/175.1, 176.1, 177.1, 227/178.1; 250/234, 235; 264/1.26; 348/65; 361/241; 600/101, 102, 104, 107, 109, 600/114, 117, 142, 160, 173, 178, 179, 182, 600/3, 309, 341, 343, 368, 407, 411, 423, 600/439, 459, 461, 462, 463, 466, 476, 600/585; 604/102.01, 164.03, 96.01, 98.01; 606/1, 10, 140, 142, 15, 151, 185, 27, 606/48, 88, 92
See application file for complete search history.

(56) References Cited

U.S. PATENT DOCUMENTS

| 3,758,199 | A | 9/1973 | Thaxter |
| 3,959,582 | A | 5/1976 | Law et al. |

(Continued)

FOREIGN PATENT DOCUMENTS

| DE | 3837248 | 5/1990 |
| EP | 1139141 | 10/2001 |

(Continued)

OTHER PUBLICATIONS

Video-optic cable endoscopy forceps, International Journal of Pediatric Otorhinolaryngology (2003) 67, 243 /246.*

(Continued)

*Primary Examiner* — Unsu Jung
*Assistant Examiner* — Serkan Akar

(57) ABSTRACT

A module for attachment to a medical instrument to scan the anatomy with a beam of radiation. The module comprising a housing suitable for insertion in the anatomy that includes a window and a fastener to attach the housing to a medical instrument, an oscillating reflector within the housing that directs a beam of radiation onto the anatomy, and a collector to receive radiation returned from the anatomy.

9 Claims, 12 Drawing Sheets

(51) Int. Cl.
  *A61B 1/04* (2006.01)
  *A61B 5/00* (2006.01)
  *A61B 17/072* (2006.01)
  *A61B 17/29* (2006.01)
  *A61B 17/34* (2006.01)
  *A61B 17/42* (2006.01)
  *A61B 17/32* (2006.01)

(52) U.S. Cl.
  CPC .............. *A61B5/0084* (2013.01); *A61B 1/043* (2013.01); *A61B 5/0071* (2013.01); *A61B 17/07207* (2013.01); *A61B 17/29* (2013.01); *A61B 17/34* (2013.01); *A61B 17/42* (2013.01); *A61B 2017/320044* (2013.01)

(56) References Cited

U.S. PATENT DOCUMENTS

| | | | |
|---|---|---|---|
| 4,082,635 A | 4/1978 | Fritz et al. | |
| 4,141,362 A | 2/1979 | Wurster | |
| 4,313,431 A | 2/1982 | Frank | |
| 4,375,818 A * | 3/1983 | Suwaki et al. | 600/463 |
| 4,379,039 A | 4/1983 | Fujimoto et al. | |
| 4,401,123 A * | 8/1983 | Baba | 600/462 |
| 4,403,273 A | 9/1983 | Nishioka | |
| 4,409,477 A | 10/1983 | Carl | |
| 4,421,382 A | 12/1983 | Doi et al. | |
| 4,524,761 A | 6/1985 | Hattori et al. | |
| 4,527,552 A | 7/1985 | Hattori | |
| 4,573,465 A | 3/1986 | Sugiyama et al. | |
| 4,576,999 A | 3/1986 | Eckberg | |
| 4,597,380 A | 7/1986 | Raif et al. | |
| 4,643,967 A | 2/1987 | Bryant | |
| 4,676,231 A | 6/1987 | Hisazumi et al. | |
| 4,760,840 A | 8/1988 | Fournier, Jr. et al. | |
| 4,763,662 A * | 8/1988 | Yokoi | 600/461 |
| 4,803,550 A | 2/1989 | Yabe et al. | |
| 4,872,458 A | 10/1989 | Kanehira et al. | |
| 4,902,083 A | 2/1990 | Wells | |
| 4,902,115 A | 2/1990 | Takahashi | |
| 4,934,773 A | 6/1990 | Becker | |
| 4,938,205 A | 7/1990 | Nudelman | |
| 5,003,300 A | 3/1991 | Wells | |
| 5,023,905 A | 6/1991 | Wells et al. | |
| 5,048,077 A | 9/1991 | Wells et al. | |
| 5,074,860 A | 12/1991 | Gregory et al. | |
| 5,078,150 A | 1/1992 | Hara et al. | |
| 5,116,317 A * | 5/1992 | Carson et al. | 604/102.01 |
| 5,163,936 A | 11/1992 | Black et al. | |
| 5,163,945 A | 11/1992 | Ortiz et al. | |
| 5,172,685 A | 12/1992 | Nudelman | |
| 5,192,288 A | 3/1993 | Thompson et al. | |
| 5,200,819 A | 4/1993 | Nudelman et al. | |
| 5,200,838 A | 4/1993 | Nudelman et al. | |
| 5,207,670 A | 5/1993 | Sinofsky | |
| 5,218,195 A | 6/1993 | Hakamata | |
| 5,251,025 A | 10/1993 | Cooper et al. | |
| 5,251,613 A | 10/1993 | Adair | |
| 5,269,289 A | 12/1993 | Takehana et al. | |
| 5,318,024 A | 6/1994 | Kittrell et al. | |
| 5,334,991 A | 8/1994 | Wells et al. | |
| 5,368,015 A | 11/1994 | Wilk | |
| 5,370,643 A | 12/1994 | Krivoshlykov et al. | |
| 5,387,197 A | 2/1995 | Smith et al. | |
| 5,393,647 A | 2/1995 | Neukermans et al. | |
| 5,427,103 A * | 6/1995 | Fujio et al. | 600/423 |
| 5,436,655 A | 7/1995 | Hiyama et al. | |
| 5,467,104 A | 11/1995 | Furness, III et al. | |
| 5,470,010 A * | 11/1995 | Rothfuss et al. | 227/177.1 |
| 5,488,862 A | 2/1996 | Neukermans et al. | |
| 5,531,740 A | 7/1996 | Black | |
| 5,540,678 A * | 7/1996 | Long et al. | 606/10 |
| 5,545,211 A | 8/1996 | An et al. | |
| 5,552,452 A | 9/1996 | Khadem et al. | |
| 5,557,444 A | 9/1996 | Melville et al. | |
| 5,562,239 A * | 10/1996 | Boiarski et al. | 227/175.2 |
| 5,590,660 A | 1/1997 | MacAulay et al. | |
| 5,596,339 A | 1/1997 | Furness, III et al. | |
| 5,608,451 A | 3/1997 | Konno et al. | |
| 5,629,790 A | 5/1997 | Neukermans et al. | |
| 5,648,618 A | 7/1997 | Neukermans et al. | |
| 5,649,952 A | 7/1997 | Lam | |
| 5,657,165 A | 8/1997 | Karpman et al. | |
| 5,658,710 A | 8/1997 | Neukermans | |
| 5,659,327 A | 8/1997 | Furness, III et al. | |
| 5,694,237 A | 12/1997 | Melville | |
| 5,701,132 A | 12/1997 | Kollin et al. | |
| 5,713,891 A | 2/1998 | Poppas | |
| 5,728,121 A | 3/1998 | Bimbo et al. | |
| 5,735,792 A | 4/1998 | Vanden Hoek et al. | |
| 5,742,419 A | 4/1998 | Dickensheets et al. | |
| 5,742,421 A | 4/1998 | Wells et al. | |
| 5,751,465 A | 5/1998 | Melville et al. | |
| 5,768,461 A | 6/1998 | Svetkoff et al. | |
| 5,797,944 A * | 8/1998 | Nobles et al. | 606/185 |
| 5,817,061 A * | 10/1998 | Goodwin et al. | 604/164.03 |
| 5,823,943 A | 10/1998 | Tomioka et al. | |
| 5,827,176 A | 10/1998 | Tanaka et al. | |
| 5,827,190 A | 10/1998 | Palcic et al. | |
| 5,833,689 A * | 11/1998 | Long | 606/48 |
| 5,841,553 A | 11/1998 | Neukermans | |
| 5,861,549 A | 1/1999 | Neukermans et al. | |
| 5,867,297 A | 2/1999 | Kiang et al. | |
| 5,895,866 A | 4/1999 | Neukermans et al. | |
| 5,903,397 A | 5/1999 | Melville et al. | |
| 5,907,425 A | 5/1999 | Dickensheets et al. | |
| 5,913,591 A | 6/1999 | Melville | |
| 5,947,930 A | 9/1999 | Schwemberger et al. | |
| 5,969,465 A | 10/1999 | Neukermans et al. | |
| 5,969,871 A | 10/1999 | Tidwell et al. | |
| 5,982,528 A | 11/1999 | Melville | |
| 5,982,555 A | 11/1999 | Melville et al. | |
| 5,993,037 A | 11/1999 | Tomioka et al. | |
| 5,995,264 A | 11/1999 | Melville | |
| 6,007,208 A | 12/1999 | Dickensheets et al. | |
| 6,008,781 A | 12/1999 | Furness, III et al. | |
| 6,013,025 A | 1/2000 | Bonne et al. | |
| 6,016,440 A | 1/2000 | Simon et al. | |
| 6,017,356 A | 1/2000 | Frederick et al. | |
| 6,017,603 A | 1/2000 | Tokuda et al. | |
| 6,024,744 A | 2/2000 | Kese et al. | |
| 6,043,799 A | 3/2000 | Tidwell | |
| 6,044,705 A | 4/2000 | Neukermans et al. | |
| 6,046,720 A | 4/2000 | Melville et al. | |
| 6,049,407 A | 4/2000 | Melville | |
| 6,056,721 A | 5/2000 | Shulze | |
| 6,057,952 A | 5/2000 | Kubo et al. | |
| 6,059,720 A | 5/2000 | Furusawa et al. | |
| 6,061,163 A | 5/2000 | Melville | |
| 6,064,779 A | 5/2000 | Neukermans et al. | |
| 6,069,725 A | 5/2000 | Melville | |
| 6,086,528 A | 7/2000 | Adair | |
| 6,086,531 A | 7/2000 | Tomioka et al. | |
| 6,088,145 A | 7/2000 | Dickensheets et al. | |
| 6,097,353 A | 8/2000 | Melville et al. | |
| 6,122,394 A | 9/2000 | Neukermans et al. | |
| 6,139,175 A | 10/2000 | Tomioka et al. | |
| 6,140,979 A | 10/2000 | Gerhard et al. | |
| 6,151,167 A | 11/2000 | Melville | |
| 6,154,305 A | 11/2000 | Dickensheets et al. | |
| 6,154,321 A | 11/2000 | Melville et al. | |
| 6,157,352 A | 12/2000 | Kollin et al. | |
| 6,166,841 A | 12/2000 | Melville | |
| 6,172,789 B1 | 1/2001 | Kino et al. | |
| 6,178,346 B1 | 1/2001 | Amundson et al. | |
| 6,179,776 B1 | 1/2001 | Adams et al. | |
| 6,191,761 B1 | 2/2001 | Melville et al. | |
| 6,192,267 B1 | 2/2001 | Scherninski et al. | |
| 6,200,595 B1 | 3/2001 | Motoyashiki et al. | |
| 6,204,829 B1 | 3/2001 | Tidwell | |
| 6,204,832 B1 | 3/2001 | Melville et al. | |
| 6,207,392 B1 | 3/2001 | Weiss et al. | |
| 6,210,401 B1 | 4/2001 | Lai | |
| 6,220,711 B1 | 4/2001 | Melville | |

(56) References Cited

U.S. PATENT DOCUMENTS

| | | |
|---|---|---|
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,296,608 B1 * | 10/2001 | Daniels et al. ............... 600/104 |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 * | 9/2002 | Knodel et al. ............... 606/151 |
| 6,454,762 B1 * | 9/2002 | Rosler et al. ................. 606/15 |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 * | 9/2004 | Hoffman ................... 227/178.1 |
| 6,795,221 B1 | 9/2004 | Urey |
| 6,802,809 B2 | 10/2004 | Okada |
| 6,803,561 B2 | 10/2004 | Dunfield |
| 6,814,699 B2 * | 11/2004 | Ross et al. .................... 600/179 |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 * | 6/2005 | Swayze et al. ............ 227/176.1 |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel |
| 6,976,994 B2 | 12/2005 | Ballou et al. |
| 6,978,921 B2 * | 12/2005 | Shelton et al. ............ 227/176.1 |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B2 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |

(56) References Cited

U.S. PATENT DOCUMENTS

| | | | |
|---|---|---|---|
| 7,367,939 B2* | 5/2008 | Smith et al. | 600/104 |
| 7,391,013 B2 | 6/2008 | Johnston et al. | |
| 7,464,847 B2* | 12/2008 | Viola et al. | 227/175.2 |
| 7,530,948 B2* | 5/2009 | Seibel et al. | 600/178 |
| 7,553,277 B2* | 6/2009 | Hoefig et al. | 600/173 |
| 7,589,316 B2* | 9/2009 | Dunki-Jacobs | 250/235 |
| 7,637,905 B2* | 12/2009 | Saadat et al. | 606/1 |
| 7,783,133 B2* | 8/2010 | Dunki-Jacobs et al. | 382/296 |
| 7,842,028 B2* | 11/2010 | Lee | 606/1 |
| 7,845,534 B2* | 12/2010 | Viola et al. | 227/175.2 |
| 7,870,989 B2* | 1/2011 | Viola et al. | 227/175.2 |
| 7,918,845 B2* | 4/2011 | Saadat et al. | 606/1 |
| 2001/0055462 A1* | 12/2001 | Seibel | 385/147 |
| 2002/0015724 A1 | 2/2002 | Yang et al. | |
| 2002/0021356 A1* | 2/2002 | Nakashima | 348/65 |
| 2002/0024495 A1 | 2/2002 | Lippert et al. | |
| 2002/0050956 A1 | 5/2002 | Gerhard et al. | |
| 2002/0075284 A1 | 6/2002 | Rabb, III | |
| 2002/0088925 A1 | 7/2002 | Nestorovic et al. | |
| 2002/0115922 A1 | 8/2002 | Waner et al. | |
| 2002/0141026 A1 | 10/2002 | Wiklof et al. | |
| 2002/0158814 A1 | 10/2002 | Bright et al. | |
| 2002/0163484 A1 | 11/2002 | Furness, III et al. | |
| 2002/0167462 A1 | 11/2002 | Lewis et al. | |
| 2002/0171776 A1 | 11/2002 | Tegreene et al. | |
| 2002/0171937 A1 | 11/2002 | Tegreene et al. | |
| 2002/0173786 A1* | 11/2002 | Kortenbach et al. | 606/45 |
| 2003/0013960 A1* | 1/2003 | Makin et al. | 600/439 |
| 2003/0016187 A1 | 1/2003 | Melville et al. | |
| 2003/0018266 A1* | 1/2003 | Makin et al. | 600/459 |
| 2003/0018270 A1* | 1/2003 | Makin et al. | 600/466 |
| 2003/0030753 A1 | 2/2003 | Kondo et al. | |
| 2003/0032143 A1 | 2/2003 | Neff et al. | |
| 2003/0034709 A1 | 2/2003 | Jerman | |
| 2003/0058190 A1 | 3/2003 | Lewis et al. | |
| 2003/0086172 A1 | 5/2003 | Urey | |
| 2003/0092995 A1 | 5/2003 | Thompson | |
| 2003/0130562 A1 | 7/2003 | Barbato et al. | |
| 2003/0142934 A1 | 7/2003 | Pan et al. | |
| 2003/0159447 A1 | 8/2003 | Sergio et al. | |
| 2003/0191459 A1* | 10/2003 | Ganz et al. | 606/15 |
| 2003/0214460 A1 | 11/2003 | Kovacs | |
| 2003/0216729 A1 | 11/2003 | Marchitto et al. | |
| 2004/0004585 A1 | 1/2004 | Brown et al. | |
| 2004/0057103 A1 | 3/2004 | Bernstein | |
| 2004/0075624 A1 | 4/2004 | Tegreene et al. | |
| 2004/0076390 A1 | 4/2004 | Dong Yang et al. | |
| 2004/0085261 A1 | 5/2004 | Lewis et al. | |
| 2004/0085617 A1 | 5/2004 | Helsel et al. | |
| 2004/0087844 A1 | 5/2004 | Yen | |
| 2004/0101822 A1 | 5/2004 | Wiesner et al. | |
| 2004/0113059 A1 | 6/2004 | Kawano et al. | |
| 2004/0118821 A1 | 6/2004 | Han et al. | |
| 2004/0119004 A1 | 6/2004 | Wine et al. | |
| 2004/0122328 A1 | 6/2004 | Wang et al. | |
| 2004/0133231 A1* | 7/2004 | Maitland et al. | 606/200 |
| 2004/0133786 A1 | 7/2004 | Tarbouriech | |
| 2004/0151466 A1 | 8/2004 | Crossman-Bosworth et al. | |
| 2004/0155186 A1 | 8/2004 | Nestorovic et al. | |
| 2004/0155834 A1 | 8/2004 | Wit et al. | |
| 2004/0179254 A1 | 9/2004 | Lewis et al. | |
| 2004/0196518 A1 | 10/2004 | Wine et al. | |
| 2004/0223202 A1 | 11/2004 | Lippert et al. | |
| 2004/0225222 A1 | 11/2004 | Zeng et al. | |
| 2004/0232197 A1* | 11/2004 | Shelton et al. | 227/175.1 |
| 2004/0236371 A1 | 11/2004 | McNally-Heintzelman et al. | |
| 2004/0240866 A1 | 12/2004 | Ramsbottom | |
| 2004/0252377 A1 | 12/2004 | Urey | |
| 2004/0254474 A1 | 12/2004 | Seibel et al. | |
| 2005/0010787 A1 | 1/2005 | Tarbouriech | |
| 2005/0014995 A1 | 1/2005 | Amundson et al. | |
| 2005/0020877 A1 | 1/2005 | Ishihara et al. | |
| 2005/0020926 A1* | 1/2005 | Wiklof et al. | 600/476 |
| 2005/0023356 A1 | 2/2005 | Wiklof et al. | |
| 2005/0030305 A1 | 2/2005 | Brown et al. | |
| 2005/0038322 A1 | 2/2005 | Banik | |
| 2005/0038423 A1* | 2/2005 | Makin et al. | 606/27 |
| 2005/0113719 A1* | 5/2005 | Saadat | 600/585 |
| 2005/0113890 A1* | 5/2005 | Ritchie et al. | 607/88 |
| 2005/0116038 A1 | 6/2005 | Lewis et al. | |
| 2005/0135749 A1* | 6/2005 | Nield et al. | 385/38 |
| 2005/0162762 A1 | 7/2005 | Novak | |
| 2005/0165272 A1* | 7/2005 | Okada et al. | 600/114 |
| 2005/0173817 A1* | 8/2005 | Fauver et al. | 264/1.26 |
| 2005/0182295 A1* | 8/2005 | Soper et al. | 600/117 |
| 2005/0187441 A1 | 8/2005 | Kawasaki et al. | |
| 2005/0203343 A1 | 9/2005 | Kang et al. | |
| 2005/0240147 A1* | 10/2005 | Makower et al. | 604/96.01 |
| 2005/0256533 A1* | 11/2005 | Roth et al. | 606/167 |
| 2006/0010985 A1 | 1/2006 | Schneider | |
| 2006/0084867 A1 | 4/2006 | Tremblay et al. | |
| 2006/0149134 A1* | 7/2006 | Soper et al. | 600/182 |
| 2006/0164330 A1 | 7/2006 | Bright et al. | |
| 2006/0173479 A1* | 8/2006 | Smith | 606/185 |
| 2006/0183246 A1 | 8/2006 | Wiesner et al. | |
| 2006/0195014 A1* | 8/2006 | Seibel et al. | 600/102 |
| 2006/0235444 A1* | 10/2006 | Huitema et al. | 606/142 |
| 2006/0238774 A1 | 10/2006 | Lindner et al. | |
| 2006/0245971 A1 | 11/2006 | Burns et al. | |
| 2006/0258901 A1* | 11/2006 | Fujimori et al. | 600/101 |
| 2006/0276807 A1* | 12/2006 | Keast et al. | 606/140 |
| 2006/0284790 A1 | 12/2006 | Tegreene et al. | |
| 2006/0287572 A1* | 12/2006 | Wimmer | 600/107 |
| 2007/0010727 A1* | 1/2007 | Van Beek et al. | 600/341 |
| 2007/0032701 A1* | 2/2007 | Fowler et al. | 600/173 |
| 2007/0038119 A1 | 2/2007 | Chen et al. | |
| 2007/0046778 A1 | 3/2007 | Ishihara et al. | |
| 2007/0093703 A1* | 4/2007 | Sievert et al. | 600/343 |
| 2007/0135770 A1 | 6/2007 | Hunt et al. | |
| 2007/0156021 A1 | 7/2007 | Morse et al. | |
| 2007/0161876 A1 | 7/2007 | Bambot et al. | |
| 2007/0162093 A1 | 7/2007 | Porter et al. | |
| 2007/0167681 A1 | 7/2007 | Gill et al. | |
| 2007/0173686 A1* | 7/2007 | Lin et al. | 600/102 |
| 2007/0173707 A1 | 7/2007 | Mitra | |
| 2007/0175947 A1* | 8/2007 | Ortiz et al. | 227/175.1 |
| 2007/0179366 A1 | 8/2007 | Pewzner et al. | |
| 2007/0197874 A1 | 8/2007 | Ishihara | |
| 2007/0197875 A1 | 8/2007 | Osaka | |
| 2007/0203413 A1 | 8/2007 | Frangioni | |
| 2007/0213588 A1 | 9/2007 | Morishita et al. | |
| 2007/0213618 A1 | 9/2007 | Li et al. | |
| 2007/0225695 A1 | 9/2007 | Mayer et al. | |
| 2007/0238930 A1 | 10/2007 | Wiklof et al. | |
| 2007/0244365 A1 | 10/2007 | Wiklof | |
| 2007/0249896 A1* | 10/2007 | Goldfarb et al. | 600/101 |
| 2007/0260121 A1 | 11/2007 | Bakos et al. | |
| 2007/0260273 A1 | 11/2007 | Cropper et al. | |
| 2007/0276409 A1* | 11/2007 | Ortiz et al. | 606/139 |
| 2007/0299309 A1* | 12/2007 | Seibel et al. | 600/117 |
| 2008/0013960 A1* | 1/2008 | Tearney et al. | 398/139 |
| 2008/0021268 A1* | 1/2008 | Shoroji et al. | 600/101 |
| 2008/0058629 A1* | 3/2008 | Seibel et al. | 600/368 |
| 2008/0071165 A1* | 3/2008 | Makin et al. | 600/411 |
| 2008/0073163 A1* | 3/2008 | Weir et al. | 188/71.1 |
| 2008/0108868 A1* | 5/2008 | Swain et al. | 600/104 |
| 2008/0147000 A1* | 6/2008 | Seibel et al. | 604/98.01 |
| 2008/0154090 A1 | 6/2008 | Hashimshony | 600/104 |
| 2008/0167521 A1* | 7/2008 | Sheetz et al. | 600/101 |
| 2008/0167546 A1* | 7/2008 | Youmans et al. | 600/407 |
| 2008/0173803 A1 | 7/2008 | Dunki-Jacobs | 250/234 |
| 2008/0221388 A1* | 9/2008 | Seibel et al. | 600/109 |
| 2008/0226029 A1 | 9/2008 | Weir et al. | 378/65 |
| 2008/0249369 A1* | 10/2008 | Seibel et al. | 600/182 |
| 2008/0255458 A1* | 10/2008 | Dunki-Jacobs et al. | 600/476 |
| 2008/0262312 A1 | 10/2008 | Carroll et al. | 600/160 |
| 2008/0269562 A1* | 10/2008 | Marescaux et al. | 600/142 |
| 2008/0291597 A1* | 11/2008 | Seibel et al. | 361/241 |
| 2008/0294023 A1 | 11/2008 | Rabinovitz et al. | 600/309 |
| 2008/0312490 A1* | 12/2008 | Cropper et al. | 600/3 |
| 2009/0024191 A1* | 1/2009 | Seibel et al. | 607/92 |
| 2009/0028407 A1* | 1/2009 | Seibel et al. | 382/131 |

(56) References Cited

U.S. PATENT DOCUMENTS

| | | | | |
|---|---|---|---|---|
| 2009/0036734 | A1* | 2/2009 | Dunki-Jacobs et al. | 600/104 |
| 2009/0182202 | A1* | 7/2009 | Vayser et al. | 600/182 |
| 2010/0185215 | A1* | 7/2010 | Huitema et al. | 606/142 |

FOREIGN PATENT DOCUMENTS

| | | |
|---|---|---|
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

International Search Report issued regarding International Application No. PCT/US2007/078868 (Mar. 28, 2008).
PCT, International Search Report, PCT/US2008/066552 (Oct. 23, 2008).
Kiang, M-H et al., "Surface-Micromachined Electrostatic-Comb Driven Scanning Micromirrors for Barcode Scanners" (date of first publication unknown).
Lewis, J.R. et al., "Scanned beam medical imager," MOEMS Display and Imaging Systems II, Proceedings of SPIE vol. 5348, pp. 40-51 (2004).
James, R. et al., "Update on MEMS-based Scanned Beam Imager" (date of first publication unknown).
Wiklof, C., "Display technology spawns laser camera," Laser Focus World (Dec. 2004).
"Press Information—Phillips' Fluid Lenses Bring Things into Focus," http://www.newscenter.philips.com (Mar. 3, 2004).
Lettice, J., "The $5 'no moving parts' fluid zoom lens—twice," The Register (Mar. 15, 2004).
"Volcano Products—IVUS Imaging Visions® PV018," http://www.volcanotherapeutics.com (date of first publication unknown).
Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).
"Crystalplex Technology—PlxBead™ Superior Qualities," http:www.crystalplex.com (date of first publication unknown).
"Microvision [illuminating information] Products/Overview, Corporate Overview Presentation 2006" (2006).
"Holographic Beam Combiner for Ladar, Printer, Fiber Optics, and Cancer Treatment," by Digital Optics Technologies, Inc., http://www.mdatechnolopy.net (date of first publication unknown).
Brown, D.M., Abstract from SPIE Digital Library for "High-power laser diode beam combiner," Optical Engineering, vol. 42, Issue 11 (2003).
Literature entitled "All fiber beam combiner from Point Source" (Oct. 13, 2006).
"Custom Polarzing Cube Beamsplitters," from GlobalSpec The Engineering Search Engine, http://www.globalspec.com (date of first publication unknown).
Literature entitled "Dallas Semiconductor MAXIM—Visible-Laser Driver has Digitally Controlled Power Modulation," by Maxim Integrated Products, http://www.maxim-ic.com (Jul. 1, 2001).
"SCAN Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).
"Bladeless Trocars," by Johnson & Johnson, http://www.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).
Ra, H. et al., "Biomedical Optics & Medical Imaging—Microtechnology enables endoscopic confocal microscopy," SPIE (http://spie.org) (2007).
Invitation to Pay Additional Fees with Partial International Search Report, PCT/US2008/074275 (Jan. 16, 2009).
Invitation to Pay Additional Fees with Partial International Search Report, PCT/US2008/074273 (Dec. 30, 2008).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US20071087930 (Jul. 3, 2008).
PCT, International Search Report, PCT/US2008/051274 (Jul. 18, 2008).

\* cited by examiner

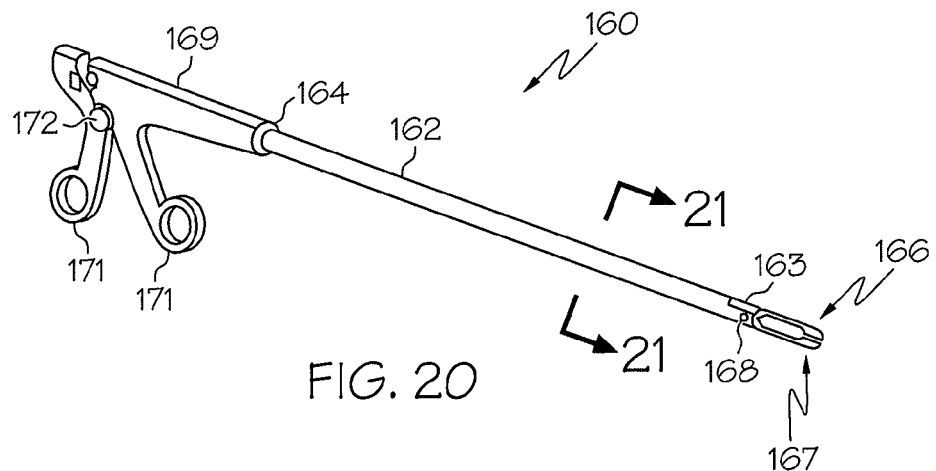
FIG. 20
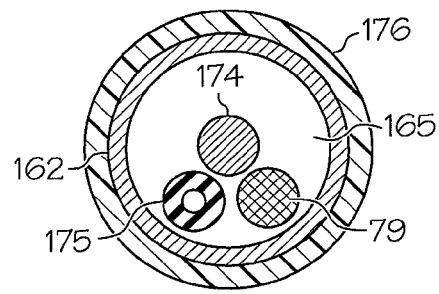
FIG. 21
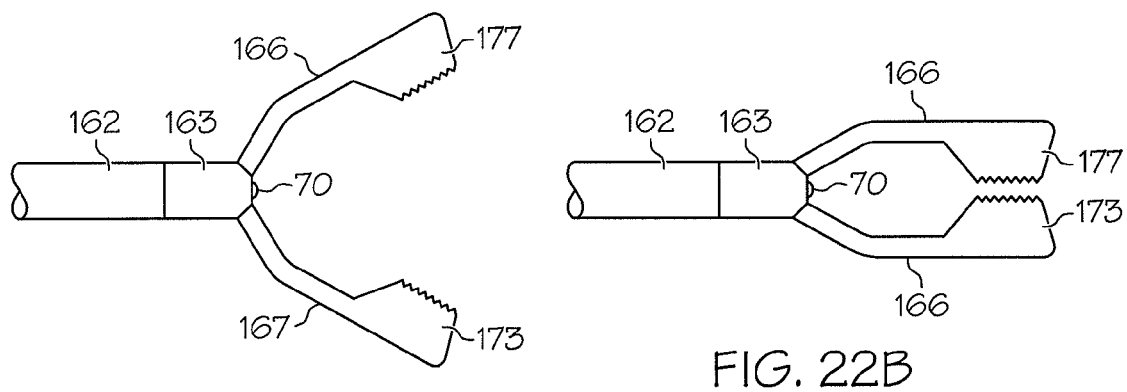
FIG. 22A
FIG. 22B

OPTICAL SCANNING MODULE AND MEANS FOR ATTACHING THE MODULE TO MEDICAL INSTRUMENTS FOR INTRODUCING THE MODULE INTO THE ANATOMY

BACKGROUND

The present application relates generally to a deployable scanning module and in particular to medical devices for deploying the scanning module within the anatomy.

U.S. Published Application 2005/0020926 discloses a scanned beam imager that may be used in applications in which cameras have been used in the past. In particular it can be used in medical devices such as video endoscopes, laparoscopes, etc.

The scanned beam imager disclosed has an illuminator that creates a first beam of light and a scanner that deflects the first beam of light across a field-of-view (FOV). The scanned beam of light sequentially illuminates spots in the FOV corresponding to various beam positions. While the beam illuminates the spots, the illuminating light beam is reflected, absorbed, scattered, refracted, or otherwise affected by the object or material in the FOV to produce scattered light energy. A portion of the scattered light energy travels to detectors that receive the light and produce electrical signals corresponding to the amount of light energy received, which is then converted to separate electrical signals. The electrical signals pass to a controller that builds up a digital image and transmits it for further processing, decoding, archiving, printing, display, or other treatment or use.

Such scanned beam imagers are a useful tool for imaging. However, the scanned beam imager may be adapted for more than just imaging. The "scanned beam imager" may be used to generate a diagnosis beam, treatment beam, or an aiming beam of radiation. The "scanned beam imager" may be made on a smaller scale than typical cameras, which will reduce the size of the incision or opening necessary to introduce the "scanned beam imager" into the anatomy. The "scanned beam imager" may be deployable itself or be incorporated into a medical instrument to reduce the number of instruments to be introduced into the body.

SUMMARY

In one aspect, disclosed herein is a module for attachment to a medical instrument to scan the anatomy with a beam of radiation. The module comprises a housing suitable for insertion in the anatomy that includes a window and a fastener to attach the housing to a medical instrument, an oscillating reflector within the housing that directs a beam of radiation onto the anatomy, and a collector to receive radiation returned from the anatomy.

In another aspect, a medical instrument for use with a scanning beam device is disclosed. The medical instrument comprises a shaft that is insertable in the anatomy, the shaft including a first working channel, and a deployable module within the first working channel of the shaft for scanning the anatomy. The deployable module comprises a housing that is suitable for insertion in the anatomy that includes a window, an oscillating reflector within the housing that directs a beam of radiation onto the anatomy, and a collector to receive radiation returned from the anatomy.

In another aspect, disclosed herein is a medical instrument for use with a scanning beam device, the medical instrument comprising a shaft that is insertable in the anatomy having a distal penetrating tip, wherein at least a portion of the shaft is transparent, and a module within the shaft to scan the anatomy. The module comprises an oscillating reflector that directs a beam of radiation on the anatomy, and a collector to receive radiation returned from the anatomy.

In another aspect, a surgical instrument for use with a scanning beam device is disclosed. The surgical instrument comprises an elongate shaft having a distal end, a proximal end, and a channel therethrough that includes a module for scanning the anatomy within the elongate shaft, a plurality of jaw members attached to the distal end of the shaft, the jaw members including grasping or cutting elements positioned in an opposed facing relationship, and a handle at the proximal end of the shaft operatively configured to open and close the jaw members. The module comprises a resonant reflector that directs a beam of radiation on the anatomy, and a collector to receive radiation returned from the anatomy.

In another aspect, disclosed herein is a surgical stapler. The surgical stapler comprises a handle portion, a shaft attached to the handle portion, an end effector distally attached to the shaft, and a firing mechanism. The handle portion is operably configured to produce a firing mechanism. The shaft transfers the firing motion to the end effector. The shaft includes a module for scanning the anatomy, which comprises a resonant reflector that directs a beam of radiation on the anatomy and a collector to receive radiation returned from the anatomy. The end effector is distally attached to the shaft that includes a plurality of surgical staples which are deployable in response to the firing motion. The firing mechanism transfers the firing motion from the handle portion to the end effector.

The details of one or more of the embodiments are set forth in the accompanying drawings and the description below. Other features, objects, and advantages of the invention will be apparent from the description and the drawings, and from the claims.

BRIEF DESCRIPTION OF THE SEVERAL VIEWS OF THE DRAWINGS

FIG. 20 is a top view of an embodiment of a surgical instrument;

FIG. 21 is a sectional view taken along line 21-21 of FIG. 20; and

FIGS. 22A and 22B illustrate enlarged perspective views of the jaw members of the surgical instrument in FIG. 20.

DETAILED DESCRIPTION

Before explaining the several embodiments disclosed herein, it should be noted that each embodiment is not limited in its application or use to the details of construction and arrangement of parts and steps illustrated in the accompanying drawings and description. The illustrative embodiments may be implemented or incorporated in other embodiments, variations and modifications, and may be practiced or carried out in various ways. Furthermore, unless otherwise indicated, the terms and expressions employed herein have been chosen for the purpose of describing the illustrative embodiments for the convenience of the reader and are not to be read as limiting.

It is further understood that any one or more of the following-described embodiments, examples, etc. can be combined with any one or more of the other following-described embodiments, examples, etc.

Figure 1:
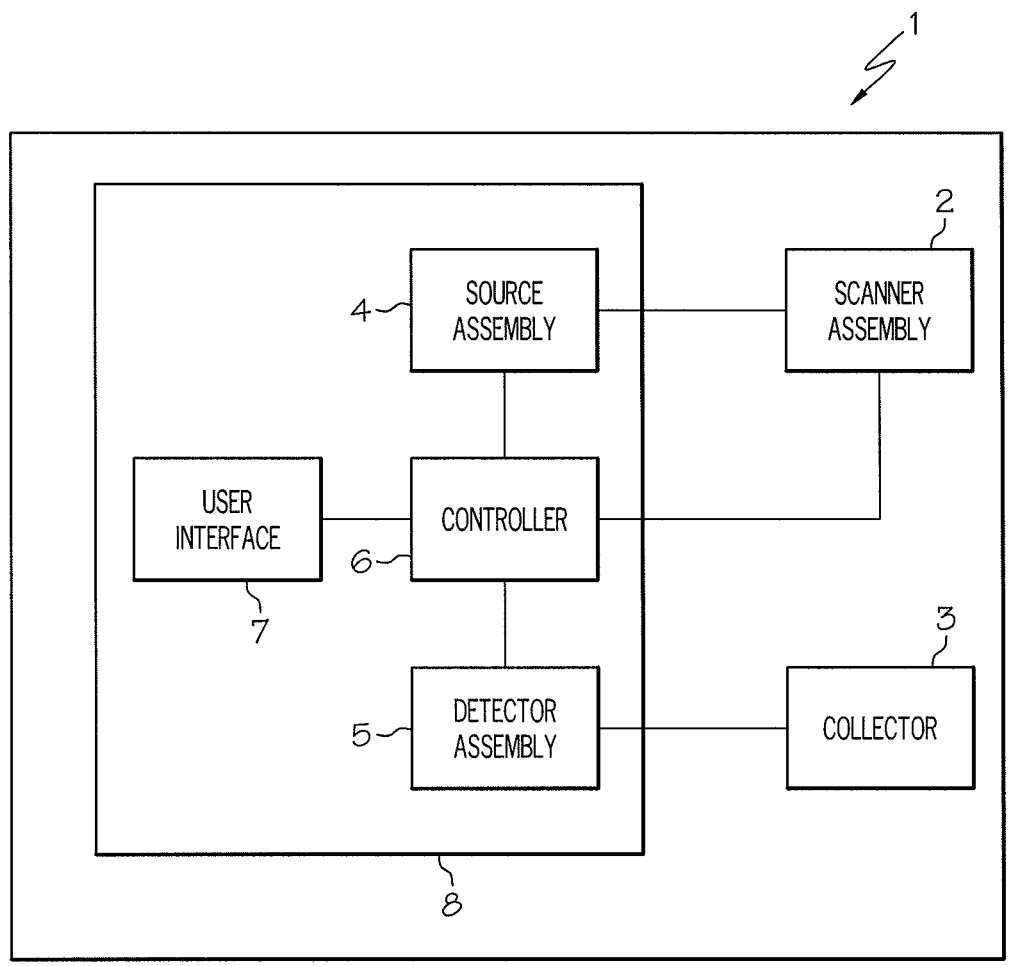
FIG. 1 is a block diagram of an embodiment of a medical device system including a scanner assembly.

Referring to FIG. 1, an embodiment of a scanning beam device 1, which may be part of a medical device, includes scanner assembly 2, collector 3, radiation source assembly 4, detector assembly 5, controller 6, and user interface 7. The radiation source assembly 4, detector assembly 5, controller 6 and user interface 7 make up functional element 8 that is known herein as a "console." The radiation source assembly 4, as selected by the user via the user interface 7, and acting through the controller 6, generates wavelengths of radiation (e.g., in the visible wavelength range or otherwise). This radiation is conveyed in a beam to scanner assembly 2, which causes the beam to be swept across an anatomical surface. The extent of this swept area is generally known as the "field of view" (FOV). Radiation returned from the scene (e.g., tissue, structures, and organs) within the FOV may be received by collector 3 and passed to detector assembly 5. The detector assembly converts the received radiation to electrical signals that are then processed by the controller to form an image on a display assembly, which in one embodiment may be included in user interface 7.

Figure 2:
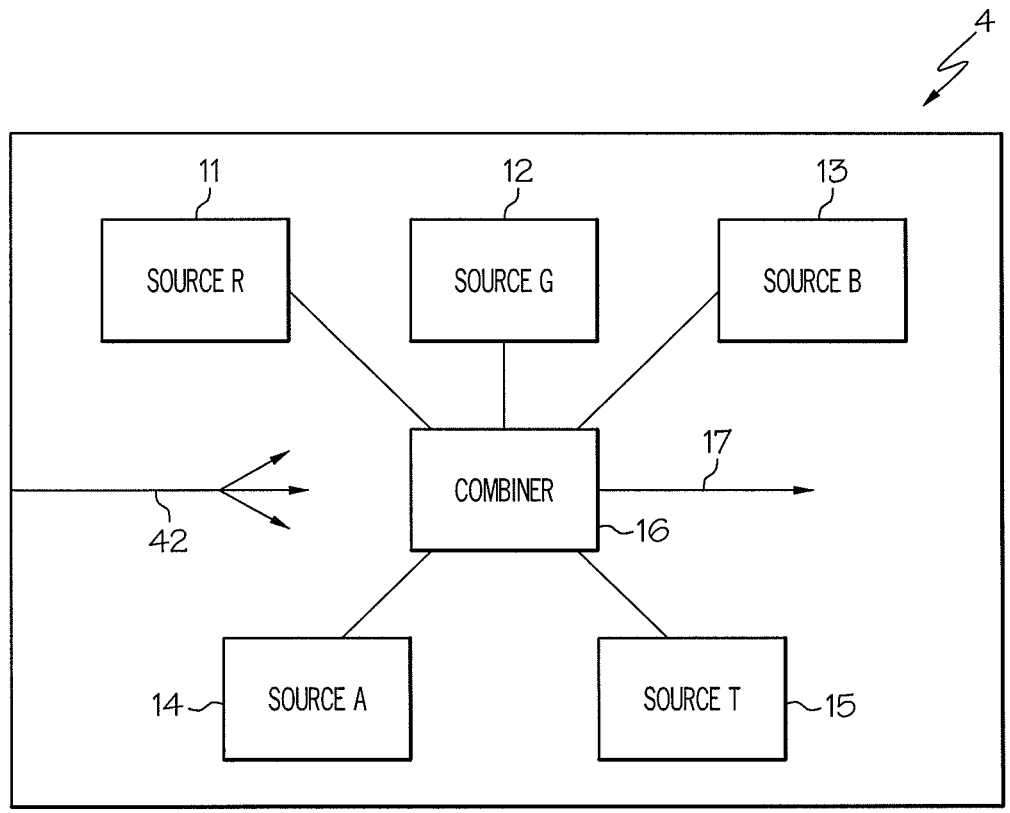
FIG. 2 is a block diagram of an embodiment of a source assembly including multiple sources for generating imaging, therapeutic and aiming beams.

FIG. 2 is a block diagram of one implementation of source assembly 4. Source assembly 4 includes multiple sources, each capable of generating radiation at a selected wavelength. Five sources are shown here, numbered 11 thru 15. It should be noted that while five sources are illustrated, there may be more or fewer sources depending, for example, on the end use. The outputs of the radiation sources 11-15, in some embodiments, may be brought together in combiner 16 to yield output beam 17. Combiner 16 may also include beam-shaping optics such as one or more collimating lenses and/or apertures. The sources may be of various types such as, but not limited thereto, light emitting diodes (LEDs), lasers, thermal sources, arc sources, fluorescent sources, gas discharge sources, or others. In some embodiments, sources 11, 12 and 13 comprise three lasers; a red diode laser, a green diode-pumped solid state (DPSS) laser, and a blue DPSS laser at approximately 635 nm, 532 nm, and 473 nm, respectively. Signals 42 may be provided by controller 6 (FIG. 1) to one or more of the sources and optionally combiner 16. Signals 42 may optionally control wavelength, power, modulation or other beam properties. The power of the beam may be modulated by a modulator, as taught in commonly assigned U.S. patent application Ser. No. 11/716,911, titled POWER MODULATION OF A SCANNING BEAM FOR IMAGING, THERAPY, AND/OR DIAGNOSIS, which is hereby incorporated by reference in its entirety.

The wavelength of radiation, for example, may be selected for imaging, therapy, or aiming. As used herein, an "imaging beam" refers to radiation selected for use in creating an image of a surface or region, a "therapeutic beam" refers to radiation selected to provide treatment of a condition such as diseased or damaged tissue, and an "aiming beam" refers to radiation selected to accentuate a portion of the FOV. In some embodiments, an additional source may provide a "diagnostic beam." A "diagnostic beam" as used herein refers to radiation selected for analysis or detection of a disease or other medical condition including, for example, to visualize the presence of (or to activate) a diagnostic marker. The diagnostic marker could be naturally occurring (e.g., auto or self fluorescence) or introduced as part of the diagnostic procedure (e.g., fluorescent dyes). The apparatus to operate such beams is disclosed in commonly assigned U.S. patent application Ser. No. 11/716,806, titled MEDICAL DEVICE INCLUDING SCANNED BEAM UNIT FOR IMAGING, THERAPY, AND/OR DIAGNOSIS, as well as the operation of treatment mapping or selecting a treatment path. This reference is hereby incorporated by reference in its entirety.

Figure 3:
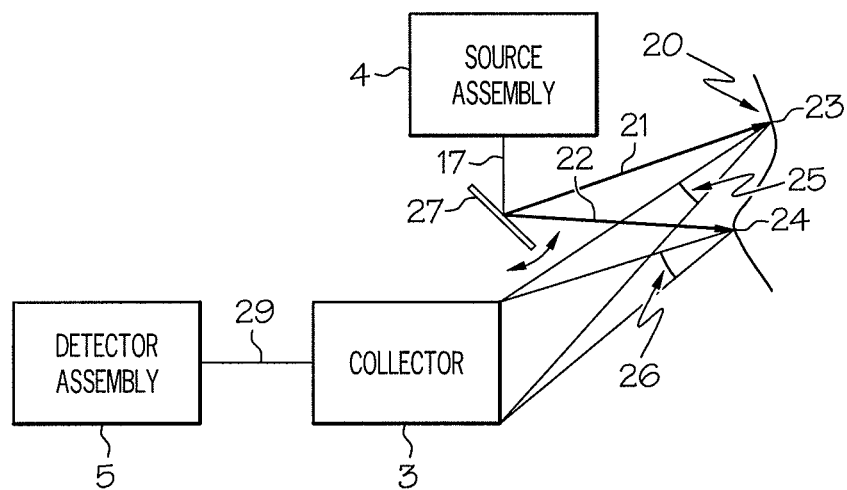
FIG. 3 is a block diagram illustrating radiation paths.

FIG. 3 illustrates the operation of device 1. Reflector 27, which is usually included in scanner assembly 2, receives a beam of radiation 17 from source assembly 4 and directs the beam onto surface 20, for example, for one or more of imaging, therapy, diagnostic, or aiming purposes. At one point in time, the beam deflected by reflector 27 is in the direction shown as 21, and impinges upon the surface to illuminate point 23. Reflector 27 oscillates in at least one axis (two axes in some embodiments), as indicated by the nearby arrowed arc, so that at some other point in time the deflected beam is in the direction indicated as 22 where, it illuminates point 24. Radiation is, in general, reflected, absorbed, scattered, refracted or otherwise affected by the properties of the surface. Radiation may leave the surface in many directions. Collector 3, however, may only receive that fraction of radiation which is returned from the surface and falls into the area subtended by its aperture. Regions 25 and 26 show the returned radiation that is captured by collector 3 when the beam is illuminating points 23 and 24 respectively. Directions 21 and 22 are not intended to represent any special part of the scan as the beam may be scanned using reflector 27 beyond them, and scans all points between them as well. Furthermore, a simplified two-dimensional view is represented by FIG. 3, and in general reflector 27 and collector 3 are adapted to illuminate and receive radiation from surfaces occupying space in three dimensions. Radiation returned from the FOV received by collector 3 is passed to detector assembly 5.

Some embodiments use a micro-electromechanical (MEMS) scanner reflector to direct the imaging, aiming and therapeutic beams onto the surface. MEMS scanner reflectors are described in, for example, U.S. Pat. No. 6,140,979, entitled SCANNED DISPLAY WITH PINCH, TIMING, AND DISTORTION CORRECTION; U.S. Pat. No. 6,245,590, entitled FREQUENCY TUNABLE RESONANT SCANNER AND METHOD OF MAKING; U.S. Pat. No. 6,285,489, entitled FREQUENCY TUNABLE RESONANT SCANNER WITH AUXILIARY ARMS; U.S. Pat. No. 6,331,909, entitled FREQUENCY TUNABLE RESONANT SCANNER; U.S. Pat. No. 6,362,912, entitled SCANNED IMAGING APPARATUS WITH SWITCHED FEEDS; U.S. Pat. No. 6,384,406, entitled ACTIVE TUNING OF A TORSIONAL RESONANT STRUCTURE; U.S. Pat. No. 6,433,907, entitled SCANNED DISPLAY WITH PLURALITY OF SCANNING ASSEMBLIES; U.S. Pat. No. 6,512,622, entitled ACTIVE TUNING OF A TORSIONAL RESONANT STRUCTURE; U.S. Pat. No. 6,515,278, entitled FREQUENCY TUNABLE RESONANT SCANNER AND METHOD OF MAKING; U.S. Pat. No. 6,515,781, entitled SCANNED IMAGING APPARATUS WITH SWITCHED FEEDS; U.S. Pat. No. 6,525,310, entitled FREQUENCY TUNABLE RESONANT SCANNER; and U.S. patent application Ser. No. 10/873,540, entitled SCANNING ENDOSCOPE; all of which are hereby incorporated by reference in their entirety.

Figure 4:
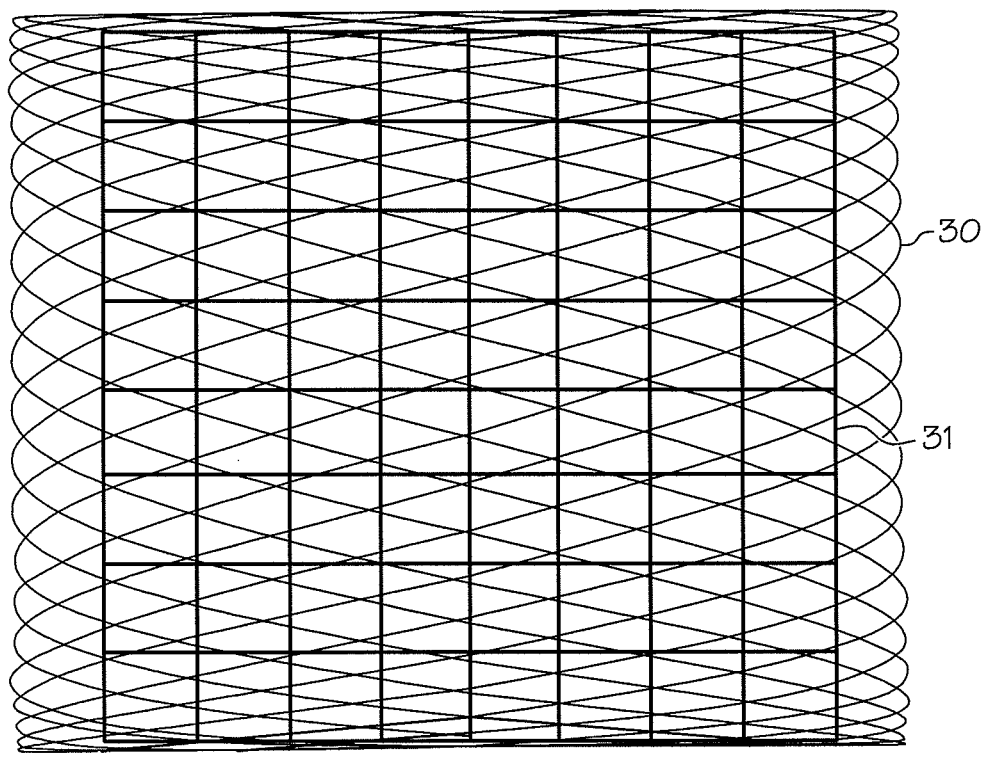
FIG. 4 is an illustration of a bi-sinusoidal scan pattern and a rectangular coordinate pattern plotted together.

Referring now to FIG. 4, in one embodiment, reflector 27 scans the beam of radiation in a pattern shown as an idealized bi-resonant or bi-sinusoidal scan pattern. High-speed MEMS reflectors and other resonant deflectors as described herein are configured and driven to execute sinusoidal angular deflections in two orthogonal axes, yielding the Lissajous pattern shown in FIG. 4. Most current display devices are configured to address display data in a Cartesian form, for example as row and column, or a particular pixel along a nearly-horizontal scan line. The bi-resonant or Lissajous scan path 30 is shown overlaid with the Cartesian or rectilinear grid 31. In the illustrated instance, the intersections between the vertical and horizontal lines of the Cartesian grid 30 represent display pixel positions while the Lissajous trace 31 represents the actual path taken by the scanned spot. As the actual scan path does not align perfectly with all the rectilinear pixel positions, these image values may be determined through interpolation. In some embodiments, registration of the Lissajous trace 30 to the Cartesian grid 31 is based on a marker that links a reference point in the scan to a point in the rectilinear matrix.

Figure 5:
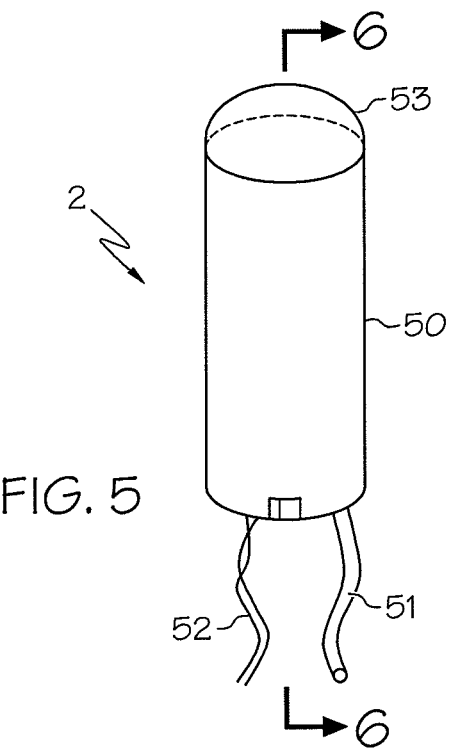
FIG. 5 is a perspective view of an embodiment of a scanner assembly.

FIG. 5 is an external view of one embodiment of the scanner assembly 2. Scanner assembly 2 includes a housing 50 that encloses the reflector 27 and other components. A source fiber 51 is used to deliver radiation from the source assembly 4 to the scanner assembly 2. Source fiber 51 may be a single mode optical fiber. In some embodiments, one or more fibers may be used to deliver imaging beams and one or more other fibers may be used to deliver a therapeutic beam (e.g., therapeutic beams having longer wavelengths, e.g., greater than 1700 nm and/or higher power). In certain embodiments, a different type of fiber, such as a holey fiber, may be used to transmit energy from the source assembly 4. In some embodiments, the same optical fiber 51 is used to deliver both the imaging beams and the therapeutic beams to the reflector, the optical fiber defining a common path for both types of beams.

Electrical wires 52 convey drive signals for the reflector 27 and other signals (position feedback, temperature, etc.) to and from controller 6 (FIG. 1). Wires 52 may also provide control and feedback connections for controlling focus characteristics of the beam shaping optic 56. In one embodiment, source fiber 51, electrical wires 52 and any other fibers or wires connected to scanner assembly 2 may be bound together into a cable (shown as 76 in FIG. 8). In one embodiment, the distal end of the scanner assembly 2 may be fitted with an optical element 53 which allows the scanned beam to illuminate the FOV. This element 53 is generally referred to and illustrated as a dome; however, its curvature, contour, and surface treatments may depend on the application and optical properties required. In some embodiments, dome 53 provides a hermetic seal with the housing 50 to protect the internal elements from the environment.

Figure 6:
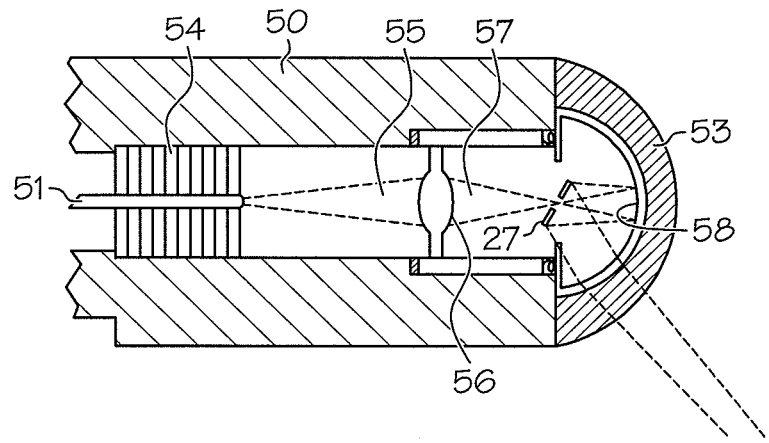
FIG. 6 is a side, section view of the scanner assembly of FIG. 5 along line 6-6.

FIG. 6 shows one embodiment for the internal components of scanner assembly 2. Source fiber 51 is affixed to the housing 50 by ferrule 54. The end of the source fiber 51 may be polished to create a beam 55 of known divergence. The beam 55 may be shaped by a beam shaping optic or lens 56 to create a beam shape appropriate for transmission through the system. After shaping, shaped beam 57 is fed through an aperture in the center of reflector 27, and then reflected off a first reflecting surface 58. First reflecting surface 58 may have a beam shaping function. Beam 57 is then directed onto reflector 27 and then out of scanner assembly 2, the details of which (in the case of an imaging beam) are described in U.S. patent application Ser. No. 10/873,540, entitled SCANNING ENDOSCOPE, the details of which are hereby incorporated by reference as if fully set forth herein. Any suitable materials can be used to form reflector 27. In some embodiments, the reflective surface of reflector 27 may be formed of gold or other suitable material for directing each of the beams including relative high energy therapeutic radiation. In other embodiments, a multilayer dielectric configuration may be used in forming reflector 27.

Scanner assembly 2 may be about 2 to about 4 millimeters by about 4 to about 10 millimeters, or any other suitable dimension. Scanner assembly 2 may by cylindrical, rectangular, or any other configuration that can be inserted into the body, or made part of an introducer. Scanner assembly 2 may be capable of being deployed within the anatomy. In one embodiment, scanner assembly 2 may enter the anatomy through a natural orifice (i.e. the mouth, anus, etc.) for a less invasive procedure.

Figure 7:
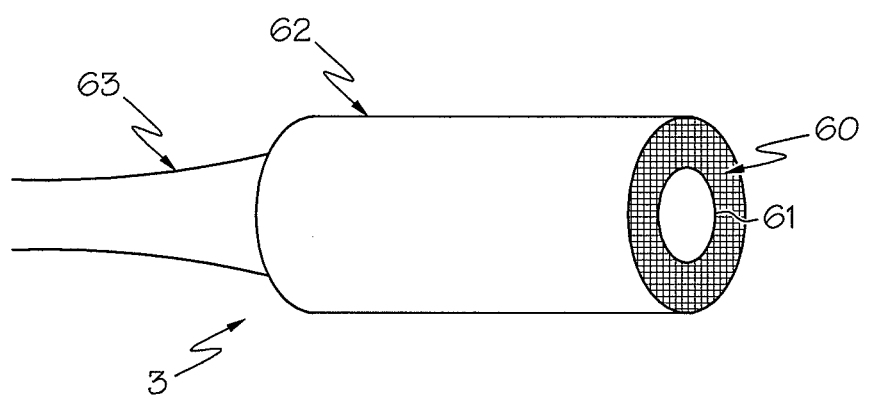
FIG. 7 is a perspective view of an embodiment of a collector.

In another embodiment, as shown in FIG. 7, collector 3 may include face 60, central void 61, covering 62, and collecting fibers 63. Radiation reflected from the FOV impinges on the face 60 of collector 3, which constitutes the receiving aperture. Face 60 may be made up of the polished ends of a large number of small diameter, multimode collecting fibers 63 which conduct the radiation to detector assembly 5 (FIGS. 1 and 3). In one embodiment, scanner assembly 2 is inserted into central void 61 of covering 62 to form a module 70 (FIG. 8) that may include a cable to connect the module 70 to the console 8 of scanning beam device 1. The cable may include the bundle of collecting fibers, the source fiber, and any other wiring for controlling scanner assembly 2 and collector 3. The fiber ends making up face 60 may be formed in a plane, or into other geometries to control the pattern of receiving sensitivity. They may be coated with diffusing or other materials to improve their angle of acceptance, to provide wavelength conversion, or wavelength selectivity. In one embodiment, detector assembly 5 may be configured to form the receiving aperture and mounted in position to receive the reflected radiation directly, without the need for a separate collector 3.

Figure 8:
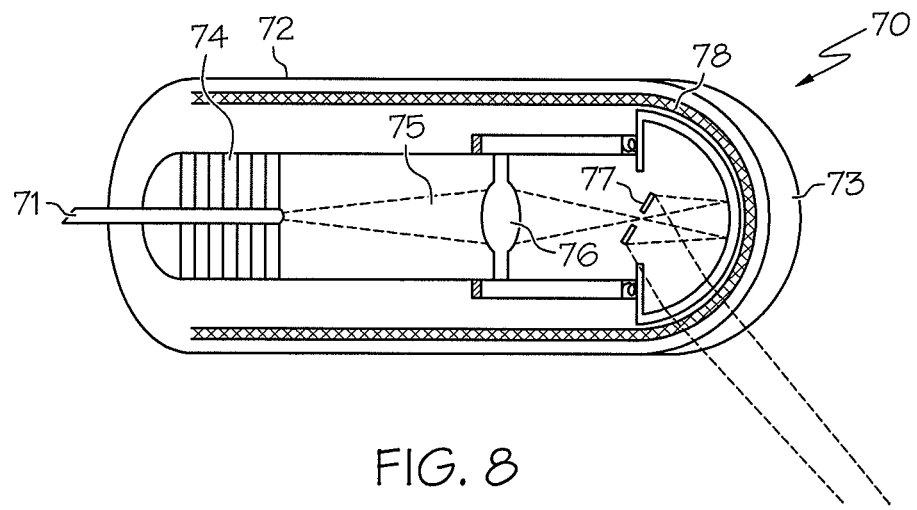
FIG. 8 is a side, section view of a module for scanning the anatomy.

Referring now to FIG. 8, one embodiment of a module 70 for imaging the anatomy using a scanning beam assembly 2 is shown. Module 70 may include an optical fiber 71, housing 72, window 73, ferrule 74, beam shaping optics 76, reflector 77, and collectors 78. Housing 72 may be made of any material suitable for insertion in the anatomy. In one embodiment, housing 72 may be metal, plastic, or a combination thereof. In one embodiment, module 70 may be deployable in the anatomy. In one embodiment, a cable may extend from the housing 72. Window 73 may have optical power and further shape the beam as it passes therethrough. In one embodiment, collectors 78 may be light collecting fibers enclosed by housing 72. Light collecting fibers may be multi-mode optical fibers that transmit the light to detector assembly 5 in console 8 (see FIG. 1) or, in some embodiments, the light collecting fibers may be replaced by optical-to-electrical converters such as photodiodes. Collector 78 receives radiation that returns from the anatomy that is scanned by the module 70.

Module 70 may be shown in several figures as a cylindrical unit; however, module 70 is not limited to that configuration. Module 70 may have an elongated form having a rectangular, square, polygonal, oval, or any other shape to the housing 72 that facilitates movement of the module through a working channel, lumen, or through a portion of the anatomy. A lumen may be a natural or manmade hollow cavity, for example a hollow cavity of a surgical instrument, or a blood vessel or other tubular organ within the anatomy, such as the esophagus, colon, or urethra. In one embodiment, module 70 may be about four millimeters in diameter and about ten millimeters long. Module 70 may have at least a 140 degree field-of-view. Module 70 may be introduced through a natural or non-natural opening into the anatomy. Module 70 may be used to visualize other structures or areas within the anatomy such as, but not limited to, regions of the gastrointestinal tract (e.g., stomach, duodenum, small intestine, colon), the respiratory tract (e.g., nose, lower respiratory tract), the urinary tract, the female reproductive system (e.g., cervix, uterus, Fallopian tubes), normally closed body cavities (e.g., abdominal or pelvic cavity, interior of a joint, organs of the chest), during pregnancy (e.g., amnion, fetus), blood vessels, peritoneal space external to organ structures, difficult to visualize areas such as the spine, etc.

Figure 9:
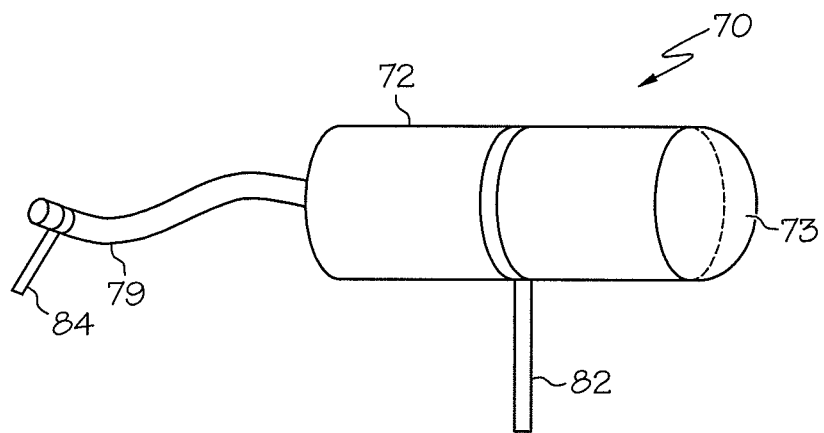
FIG. 9 is a perspective view of an embodiment of a module including fasteners.

FIG. 9 illustrates another embodiment of module 70 including housing 72, window 73, and cable 79. The module 70 may include a first fastener 82 and a second fastener 84. First fastener 82 may be attached to housing 72 to enable housing 72 to be attached to a medical instrument. Second fastener 84 may be attached to cable 79 to enable cable 79 to be attached to the medical instrument. First fastener 82 and second fastener 84 may be the same type of fastener. The fasteners 82 and 84 may be strips or wires that will wrap around the medical instrument, or clips, magnets, adhesive, adhesive coated bands, hook-and-loop or mushroom fabric, etc. to secure the housing 72 against the instrument. The fasteners may be metal, plastic, biomaterial, or any other material suitable for entry into the anatomy. In one embodiment, the fasteners may be Mylar strips. In one embodiment, the first and second fasteners 82 and 84 may remain attached to the module 70 so that the module 70 may be attached to various medical instruments. In another embodiment, the first and second fasteners 82 and 84 may be removable from module 70.

Figure 10A:
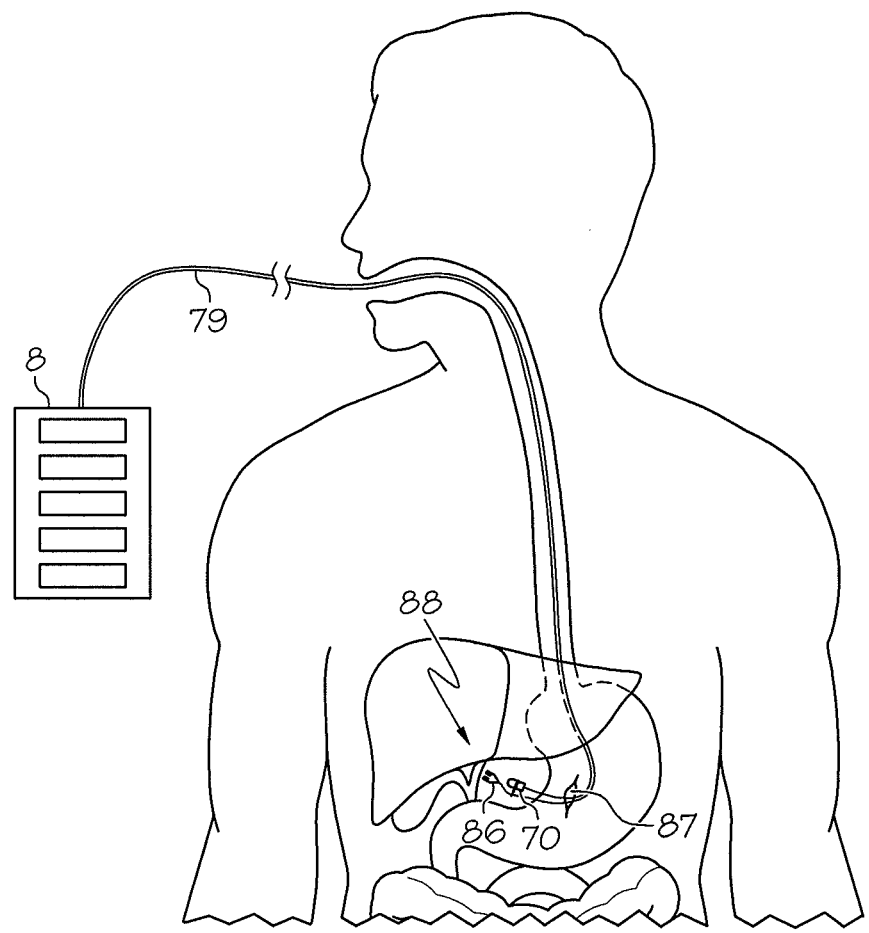
FIGS. 10A-10C illustrate a module being introduced into the anatomy by a medical instrument.
Figure 10B:
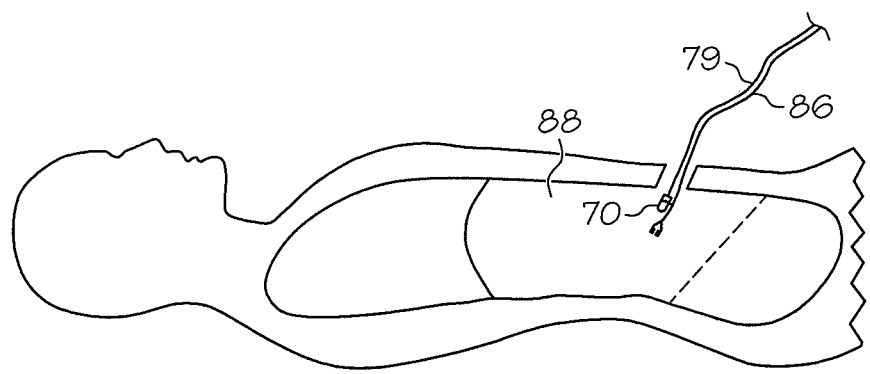
Figure 10C:
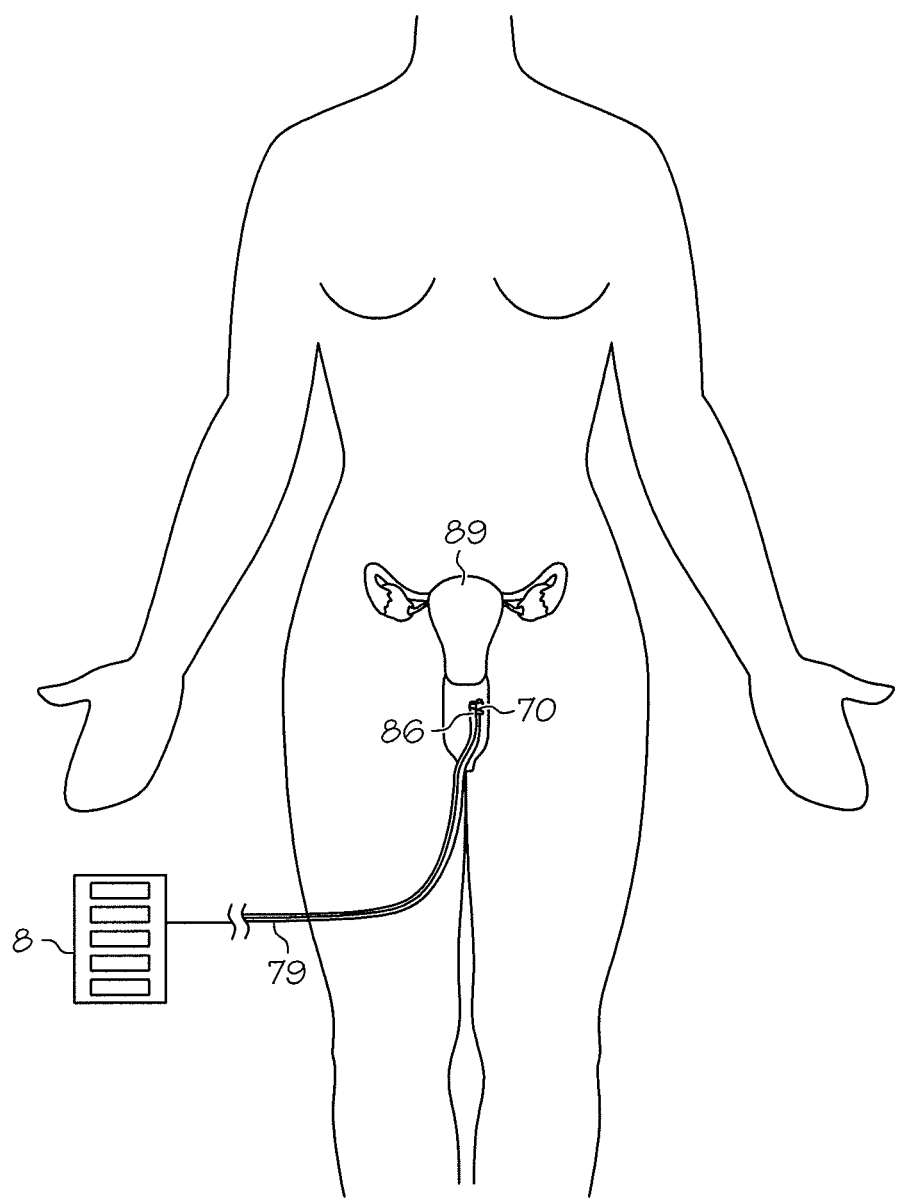

As illustrated in FIGS. 10A-10C, the first and/or second fasteners 82 and 84 of module 70 may be attached to a medical instrument 86 and introduced into the anatomy. For example, the medical instrument 86 may be a laparoscope, gastroscope, colonoscope, surgical stapler, grasper, catheter, ultrasonic, RF instrument, surgical clip applier, the instrument for inserting GERD fasteners, or any other surgical instrument. The module 70 is of such a reduced size that the overall size of the instrument is less than those medical instrument including CCD or CMOS focal plane arrays. In one embodiment, as shown in FIG. 10A, the medical instrument 86 may be a cutting tool, or other surgical tools for conducting trans-luminal and trans-gastric surgeries. The cutting tool 86 may open a port 87 through a portion of the anatomy, and with the module 70 attached thereto, the tool may be moved through the port 87 carrying module 70. In FIG. 10A, the cutting tool is illustrated as being introduced through the esophagus into the stomach where the cutting tool 86 opens a port 87 through the stomach into the peritoneal cavity 88 and then cutting tool 86 carries module 70 into the peritoneal cavity 88. The module 70 has a cable 79 extending therefrom to link the module to console 8. In another embodiment, cutting tool 86 may open the port 87 and a separate transluminal tool with module 70 attached via the first fastener 82 and/or the second fastener 84 may carry module 70 through the port 87. In another embodiment, the module 70 may be introduced into the anatomy by the cutting tool 86 through a lumen. In another embodiment for FIGS. 10A-10C, the cutting tool 86 or any other medical instrument carrying module 70 may be introduced into the anatomy through a working channel of another medical instrument, such as an endoscope. In yet another embodiment, module 70 may be moved through the port 87 independently of the cutting tool 86 or any other tool. The part of the anatomy to be cut may need to be held taunt or still during the cutting, and another medical instrument may be needed to hold that part of the anatomy. The medical instrument that holds the anatomy taunt may be included in a specialized transport tool that includes the cutting tool 86 and the module 70 attached together.

In FIG. 10B, module 70 is illustrated as being introduced into the anatomy laparoscopically. As illustrated, the module 70 may be introduced into the peritoneal cavity 88 by a medical instrument 86, such as a grasper, biopsy tool, cutting tool, clip applier, etc. In another embodiment, a trocar may be used to open a channel into the peritoneal cavity 88 or other part of the anatomy through which the medical instrument 86 carrying the module 70 may be introduced. The module 70 and the cable 79 extending therefrom may be fastened to the medical instrument by a first fastener and a second fastener as described above. Similarly, FIG. 10C illustrates a gynecological entry of module 70 into the anatomy by a medical instrument 86 to which the module is attached. As illustrated the module 70 is carried into the uterus 89 by the medical instrument 86. The medical instrument may be an endoscope or other medical instrument listed above. A cable 79 may be extending from module 70 to link the module 70 to console 8.

Figure 11:
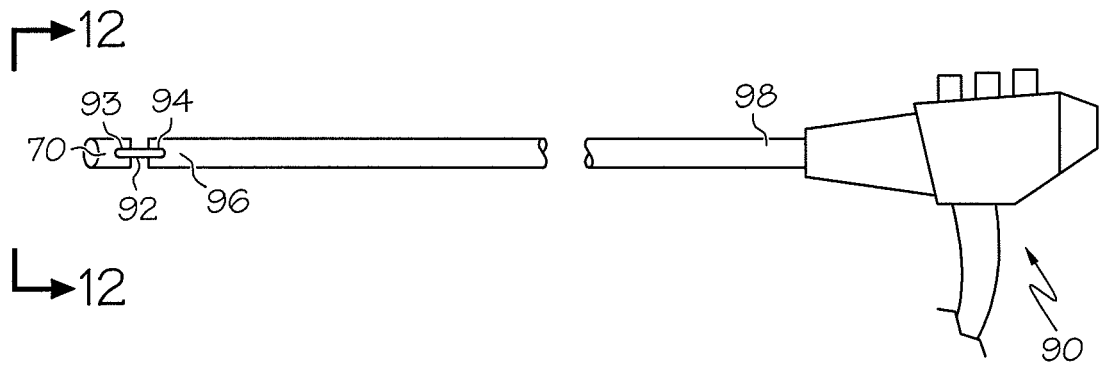
FIG. 11 is a side view of a medical instrument with a module attached to the distal end thereof.

In one embodiment, as illustrated in FIG. 11, module 70 may be attached to a medical instrument 90 by a linkage 92 having a distal end 93 and a proximal end 94. The distal end 93 of the linkage 92 may be attached to the housing of module 70 and the proximal end 93 of the linkage 92 may be attached to the medical instrument 90. The medical instrument 90 having a distal end 96 and a proximal end 98. In one embodiment, the medical instrument 90 may be an endoscope, as illustrated in FIG. 11, or any other medical instrument. In one embodiment, module 70 may extend from the distal end of the medical instrument 90 inline with the medical instrument 90. Module 70 may be pivotally attached to the medical instrument 90.

The medical instrument may be a surgical clip applier that has a module 70 mounted similarly, such that the portions of the anatomy to be clipped together may be scanned by module 70 before being clipped together. Several embodiments of surgical clip appliers are described in U.S. Pat. Nos. 5,163,945, 5,192,288, and 6,520,972, which are herein incorporated by reference.

Figure 12:
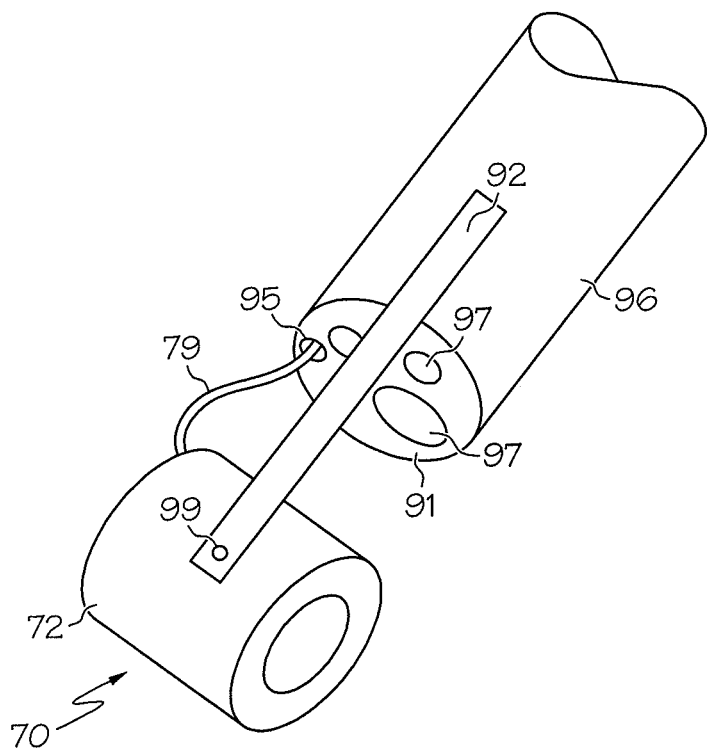
FIG. 12 is a perspective view of the distal end of the medical instrument of FIG. 11 along line 12-12.

FIG. 12 is an end view of one embodiment of medical instrument 90 from FIG. 11. In the embodiment illustrated, linkage 92 may be pivotally attached to housing 72 of module 70, by a pivot 99. Cable 79 may extend from housing 72. Cable 79 may enter the distal end 96 of the medical instrument through a port 95. Port 95 may be any shape and in any location on the distal end of the medical instrument including the end face 91 or the side of the distal end 96. The medical instrument 90 may include a working channel 97. The working channel 97 may vary in size and shape as needed to fit the desired instrument(s) to be fed through the channel. Module 70 may be rotated about the pivotal attachment to the housing 72 to a plurality of positions for scanning the anatomy. Module 70 may rotate relative to pivot 99 from being inline with the medical instrument 90. When module 70 rotates from the inline position a space is opened between module 70 and the end face 91 of the medical instrument 90 such that the working channel(s) 97 may be used by other medical tools while module 70 scans the anatomy.

In one embodiment, cable 79 may be affixed to an elastic member (not shown in FIG. 12) that is attached to the medical instrument within port 95 near the end face 91. The elastic member may run parallel to or encase a portion of cable 79 proximal to module 70 such that the elastic member is stressed when the module 70 rotates from the inline position. The stress on the elastic element can then retract cable 79 into port 95 when the module 70 returns to the inline position.

Figure 13:
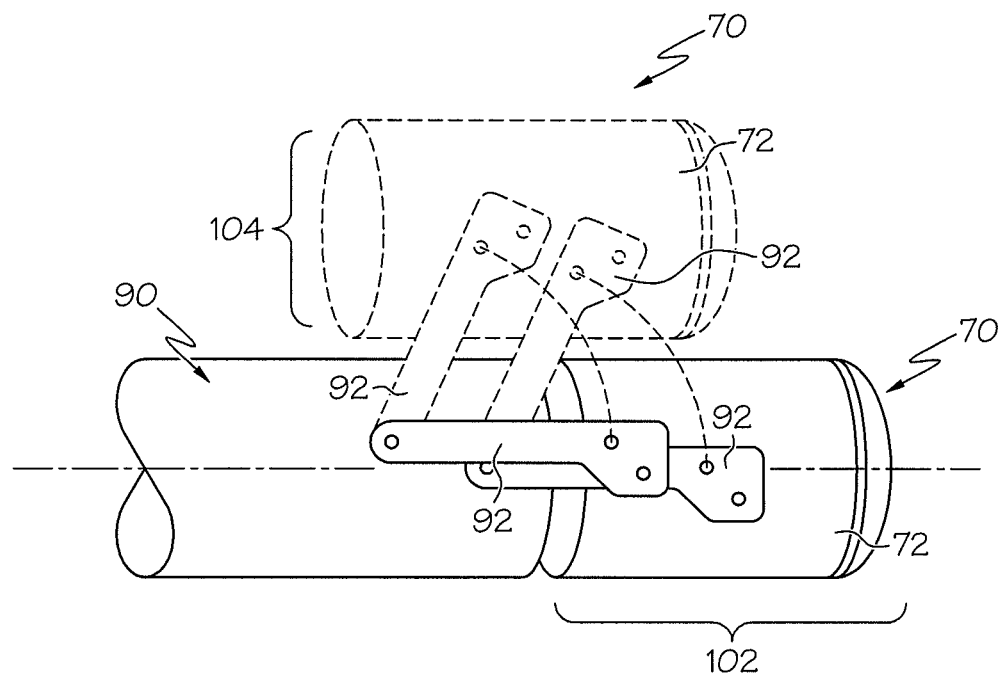
FIG. 13 is a side perspective view of a module capable of occupying a first position along the longitudinal axis of the medical instrument and a second position offset therefrom.

In another embodiment, as shown in FIG. 13, module 70 may include a linkage 92 between the module 70 and the medical instrument 90. The linkage 92 may be pivotally attached to the module 70 and may be pivotally attached to the medical instrument 90. The linkage 92 may move module 70 from being along the longitudinal axis of the medical instrument 90 (i.e., being inline 102 with the medical instrument 90) to being offset 104 from the longitudinal axis of the medical instrument 90. The module 70 may have a plurality of offset positions. In another embodiment, module 70 may be tilted (i.e., angled or aimed) while offset from of the medical instrument 90. In one embodiment, the linkage may be an arm or a plurality of arms. In another embodiment, the member may be a 4-bar linkage. The member(s) may be in any arrangement (proportions of the members, placement of the members, placement of the pivots, etc.) to enable a variety of positions and orientations of the module 70 in relation to the distal end of the medical instrument 90.

In one embodiment, the linkage 92 keeps the module 70 in a first position 102 (along the longitudinal axis of the medical instrument 90) for ease of entry of the module 70 and medical instrument 90 into the patient's anatomy. Once the module 70 and medical instrument 90 are in the anatomy, the module 70 may be moved or rotated relative to the distal end of the medical instrument 90 to provide access to the anatomy through the working channels 97 on the medical instrument 90 for other surgical tools. The small size of the module 70 allows the medical instrument 90 to carry the module 70 to or through narrow lumen or apertures.

Figure 14:
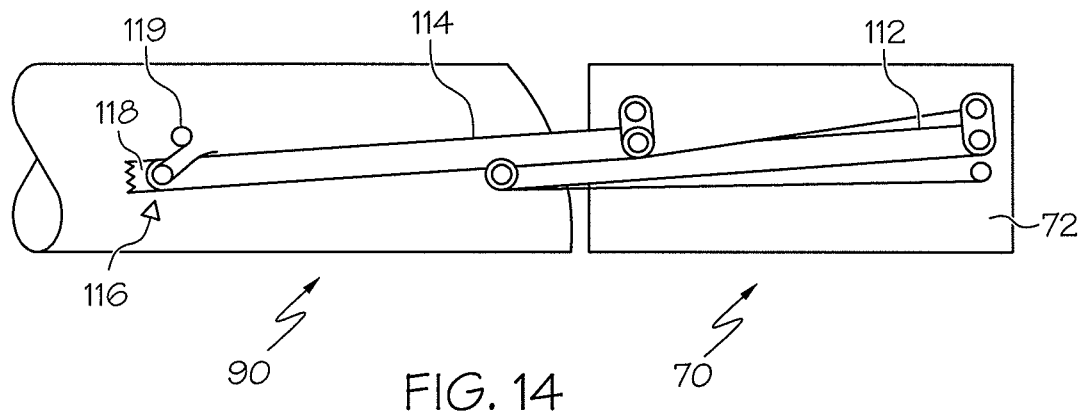
FIG. 14 is a side perspective view of a module and medical instrument connected by a first linking member and a second linking member.

In another embodiment, as shown in FIG. 14, the linkage 92 may include a first linking member 112 and a second linking member 114 designed to move the module 70 from the first position 102 (along with the longitudinal axis of the medical instrument 90) to any number of offset or second positions 104 in which the module 70 is offset from the longitudinal axis of the medical instrument 90. In one embodiment, the first linking member or the second linking member 112, 114 may include an actuator as a portion of the member. The actuator may be a shape memory actuator. The shape memory actuator enables the movement of the module 70 from being in the first position 102 (inline with the medical instrument 90) to being offset 104 therefrom. The shape memory actuator may be a shape memory alloy, which applies a lifting force to move the module. In one embodiment the shape memory actuator applies the lifting force when current (DC current) passes through the shape memory alloy. The current causes the shape memory alloy to contract, which creates the lifting force. When the current is maintained the shape memory alloy will remain in the contracted state, which will hold the module 70 in the offset position. In another embodiment, the first linking member or the second linking member may include a spring.

A "shape memory alloy" or SMA is broadly defined as a metal-based alloy having a reversible solid-state transformation typically known as a martensitic transformation. Such materials typically exhibit the shape-memory effect and superelasticity distinct from conventional metals and alloys. These materials may be ferrous or non-ferrous martensites. Such materials include, but are not limited to, iron-based alloys, copper-based alloys, and nickel-titanium alloys. Ferrous systems include, but are not limited, iron and at least one of manganese, silicon, chromium and nickel, such as iron-manganese-silicon alloys and iron-chromium-nickel alloys. Copper-based systems are typically derived from copper-zinc, copper-aluminum, and copper-tin systems. Copper systems include, but are not limited to, copper and at least one of zinc, aluminum and nickel, such as copper-zinc-aluminum alloys, copper-nickel-aluminum alloys, and copper-beryllium-aluminum alloys. Nickel based systems include, but are not limited to nickel and at least one of titanium, copper, niobium, palladium, zirconium, and hafnium. A commonly used nickel based shape memory alloy is known as Nitinol.

In another embodiment, a holding member 116, as shown in FIG. 14, may engage a detent 118 in the first and/or the second linking members 112, 114 to hold the module 70 in the offset position after the module has been moved to that position. The holding member 116 may be any shape, size, or design that will be able to engage the first and/or the second linking members 112, 114 and hold the module in the offset position. In one embodiment, the holding member 116 may be wedge shaped. Holding member 116 may protrude from within module 70 or may be attached to the exterior of the module 70. Holding member 116 may be bimetallic such that the passage of current through the holding member 116 may move the holding member 116 to engage or disengage the detent 118.

In another embodiment, the first and/or the second linking member 112, 114 may include a spring 119 to move the module 70 from the offset position back to being inline with the medical instrument 90. The spring 119 can move the module 70 when no current is flowing into the shape memory alloy included in the first linking member 112 because the lifting force of that linking member will be removed or when the holding member 116 is disengaged from the detent 118. The spring may be a hairspring. The spring stores energy when the module 70 is moved from being inline with the medical instrument to being offset therefrom that can later be used to move the module 70 back to the inline position.

Figure 15:
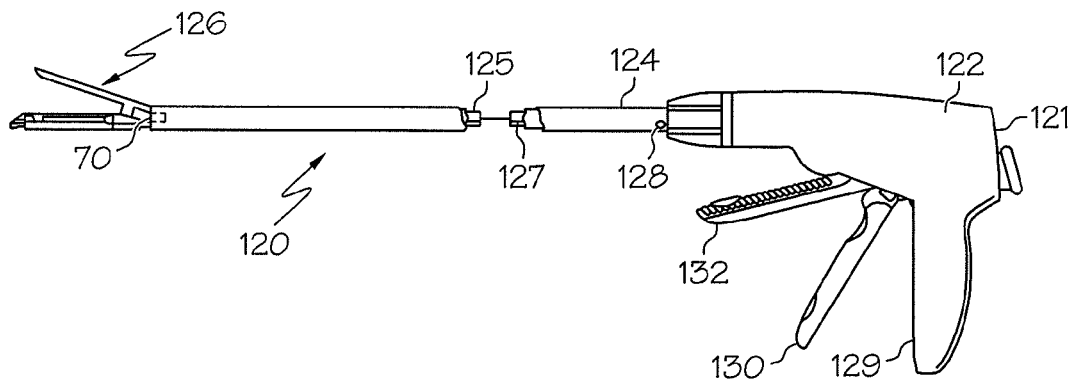
FIG. 15 illustrates a partially cut-away side elevation view of a surgical stapling instrument in an open position.

In another embodiment, as illustrated in FIG. 15, a medical instrument 120 may include a shaft 124 that is insertable into the anatomy, has a working channel 127, and includes a module 70 within the working channel 127. In one embodiment, the module 70 may be mounted within the working channel. In another embodiment, the module 70 may be capable of being released or deployed from the working channel into the anatomy. In one embodiment, the medical instrument 120 may be a surgical stapler 121. The surgical stapler 121 may include a handle portion 122 operably configured to produce a firing motion, a shaft 124 attached to handle portion 122 for transferring the firing motion, an end effector 126 distally attached to shaft 124 and responsive to the firing motion, and a firing mechanism responsive to the firing motion that transfers the firing motion to end effector 126. In one embodiment, surgical stapler 121 includes firing drive member 125 to transfer the firing motion from handle portion 122 to end effector 126. In some embodiments, end effector 126 may have an E-beam firing bar that advantageously controls the spacing of end effector 126. Further examples and embodiments of surgical stapler 121 are given in U.S. Pat. Nos. 6,978,921, 6,786,382, and 6,905,057, which are herein incorporated by reference.

Handle portion 122 may include a grip 129 toward which a closure trigger 230 may be pivotally drawn be the user to cause clamping or closing of the end effector 126. Firing trigger 132 may also be included in handle portion 122. Firing trigger 132 may be pivotally drawn toward grip 129 to cause the end effector to respond to the firing motion. During use, closure trigger 132 is actuated first. Once the user is satisfied with the positioning of the end effector 126, which may be displayed on a display system using module 70, the user may draw back closure trigger 130 to its fully closed, locked position proximate to grip 129. Then, firing trigger 132 is actuated. Firing trigger 132 springedly returns when the user removes pressure.

Shaft 124 includes channel 127 having a distal end toward end effector 126 and a proximal end toward handle portion 122. A port 128 enters channel 127 near handle portion 122. Channel 127 and port 128 are to receive module 70 therein. In one embodiment, the housing of module 70 may be adapted to securedly fix module 70 into the distal end of channel 127.

Using module 70, the user of the scanning beam device 1 may image, diagnose, treat, and/or confirm treatment of the anatomy where the instrument is directed. The scanning beam device 1 may image and confirm the placement and operation of the medical instrument 120. For example, if the instrument is a surgical stapler, module 70 may be fed through channel 127 to scan the tissue to be stapled, used to diagnose what tissue needs to be stapled, used to confirm that tissue was inserted into the stapler, used to confirm that the stapler functioned properly and that the tissue was stapled completely, or any combination thereof.

Figure 16:
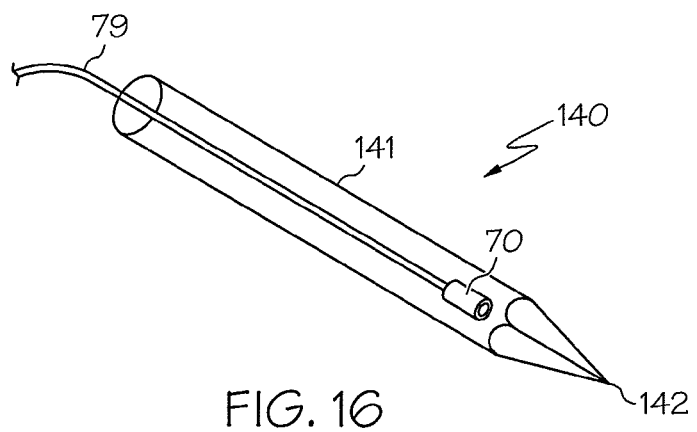
FIG. 16 is a perspective view of a trocar including a module.

In another embodiment, as shown in FIG. 16, medical instrument 140 includes shaft 141 having a distal penetrating tip 142, module 70 within shaft 141 near penetrating tip 142 to scan an area of a body. Cable 79 may extend from the shaft 141. Medical instrument 140 may include a needle or a rigid or flexible trocar. In one embodiment, distal penetrating tip 142 is transparent to enable module 70 to scan an area within the body where penetrating tip 142 has penetrated the body. In another embodiment the penetrating tip includes a window through which module 70 may scan an area within the body. The penetrating tip 142 may be used to penetrate the skin, a body cavity, a lumen, a natural body opening, or an organ. In another embodiment, medical instrument 140 may include a working channel through which other instruments may be introduced into the anatomy. Medical instrument 140 is advantageous because the penetrating tip 142 may be small enough that no post operative closure is needed (i.e., stitches). In another embodiment, the window 73 of module 70 (FIG. 8) may be built into the penetrating tip 142 or the shaft 141 of the medical instrument 140. Possible embodiments of trocars are described in U.S. Pat. No. 5,797,944, which is herein incorporated by reference.

Figure 17:
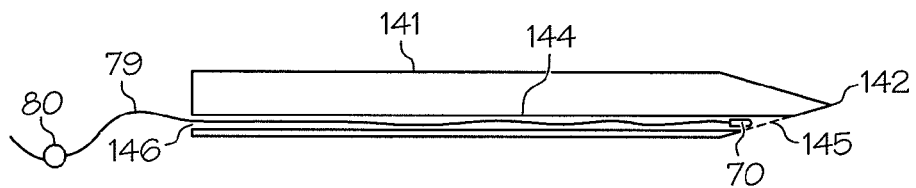
FIG. 17 is a section view of an embodiment of a trocar including a module within a channel of the trocar.

In another embodiment, as shown in FIG. 17, medical instrument 140 may include a channel 144 having a distal opening 145 and a proximal opening 146. In one embodiment, module 70 may be within channel 144 and may include cable 79 extending from the proximal opening 146. Module 70 may be fed through channel 144 to a point near the distal opening 145 while remaining in channel 144 when the penetrating tip is pushed into the anatomy. After penetrating tip 142 is within the anatomy, module 70 may be deployed therein. Medical instrument 140 may be left in place after deploying module 70 or may be removed with module 70 remaining within the anatomy. A rod or plunger may be used to deploy the module 70 through the channel 144 within the medical instrument 140 into the anatomy to deploy the module. Module 70 may then be secured within the anatomy by applying tension to cable 79. The tension may pull module 70 back against the skin, tissue, bone, or muscle near the point of penetration into the anatomy to secure module 70 in place. The tension may be applied by a counter weight 80 attached to cable 79. In another embodiment, a removable or temporary adhesive may be placed on module 70 to secure the module 70 within the anatomy. If module 70 is deployed within a lumen (i.e., esophagus, colon, urethra, etc.), the module may be secured within the body by the connecting structures disclosed in U.S. patent application Ser. No. 11/749,188 METHODS FOR IMAGING THE ANATOMY WITH AN ANATOMICALLY SECURED SCANNER ASSEMBLY, which is incorporated herein by reference.

Figure 18:
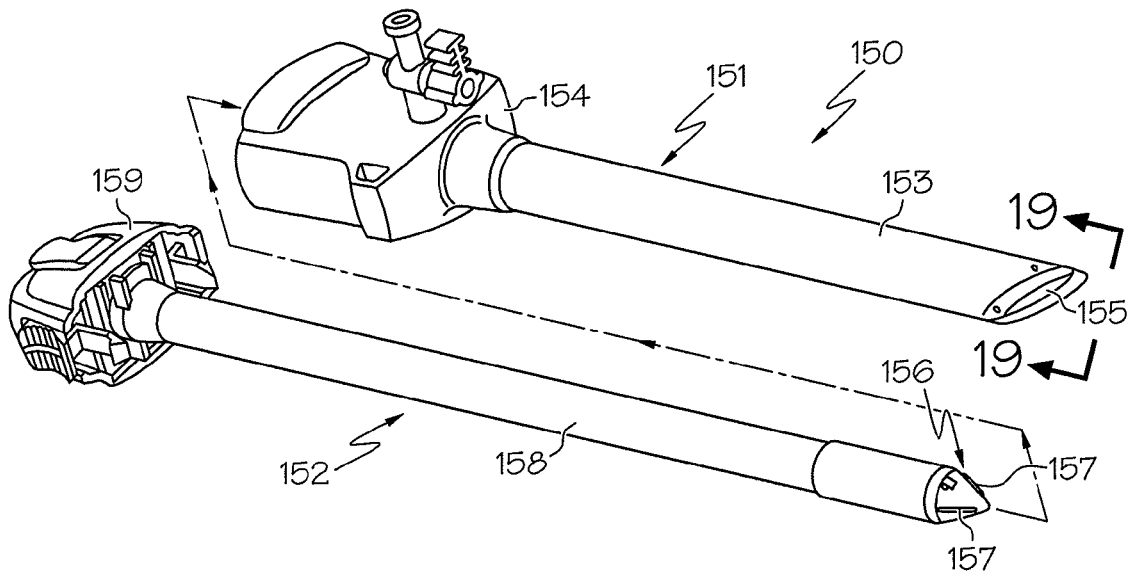
FIG. 18 is an exploded perspective view of an embodiment of a trocar.
Figure 19:
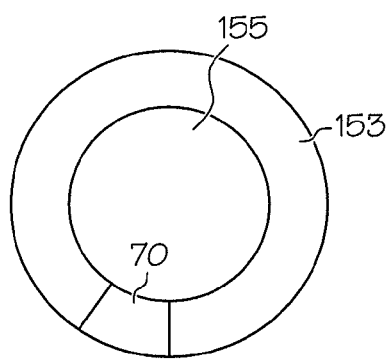
FIG. 19 is an end plan view taken along line 19-19 of FIG. 18.

In another embodiment, as illustrated in FIG. 18, a trocar 150 may include cannula 151, obturator 152, and a module 70 within the cannula 151. Cannula 151 includes sleeve 153 having a distal end and a proximal end, cannula housing 154, and a passageway 155 therethrough. For embodiments of the trocar 150, the portion of the instrument closest to the operator or user will be referred to as "proximal" and the portion farther away from the operator will be referred to as "distal." Passageway 155 may receive various members like obturators, endosurgical instrument and the like. In one embodiment, as shown in FIG. 19, sleeve 153 includes module 70 in the distal end. In one embodiment, module 70 may be shaped to conform to the sleeve 153. Module 70 may be mounted within sleeve 153 using any form of attachment.

In one embodiment, the obturator 152 may include penetrating tip 156, retractable blades 157, shaft 158, and an obturator handle 159. Obturator 152 may be capable of being inserted into and withdrawn from the cannula 151. When the obturator shaft 158 is fully inserted within the cannula 151, handle 159 mates and locks within cannula housing 154 and penetrating tip 156 of the obturator 152 protrudes from sleeve 153. Other embodiments for trocars are disclosed in U.S. Pat. Nos. 5,387,197; 5,817,061; 5,947,930, 6,017,356 all of which are incorporated herein by reference. For natural orifice transluminal endoscopic surgery (NOTES procedures), the trocar sleeve will probably have a flexible sleeve and the distal tip of the trocar could be all or part of the module that is attached as described in commonly assigned U.S. patent application Ser. Nos. 11/382,173 and 11/382,182, which are herein incorporated by reference. The flexible trocar sleeve and the elongate flexible obturator may include at least two regions of differing rigidity to facilitate positioning the trocar translumenally. In one embodiment, the trocar may include a cutting element having at least one blade. The cutting element may be formed on an outer surface of the distal tip. The blade may have a sharp, linear edge. The distal tip of the trocar may also include a paddle extending outward from an outer surface of the distal tip and configured to be rotated to separate tissue.

FIG. 20 illustrates another embodiment configured as a surgical instrument 160 that may be utilized in surgical procedures that includes a module 70. The surgical instrument 160 includes an elongated shaft 162, the shaft 162 having a distal end 163, a proximal end 164, and a channel 165 (FIG. 21). Surgical instrument 160 further includes a first and a second jaw member 166,167 that may be movably or pivotally disposed on distal end 163 of elongated shaft 162 such that they pivot about a pivot pin, rivet, screw, or the like 168 which is also fixed to the distal end 163 of elongated shaft 162. Surgical instrument 160 further includes handle 169 at the proximal end 164 of elongated shaft 162. Other embodiments for graspers are disclosed in U.S. Pat. Nos. 5,728,121 and 6,024,744, which are incorporated herein by reference.

Handle 169 includes handle members 171. Handle members 171 being pivotally connected about a pivot pin, rivet, or screw, or the like 172. At least one of handle members 171 is connected to the jaw members 166,167 by wire member 174, shown in FIG. 21, disposed through the channel 165 of elongated member 162. Wire member 174 is connected at one of its ends to at least one of handle members 171 and at its other end to a suitable endoscopic actuating mechanism (not shown) for actuating the jaw members 166,167 such that pivoting of the handle member 171 about the pivot pin, rivet, or screw 172 causes the jaw members 166,167 to open and close relative to each other. Suitable endoscopic actuating mechanisms are numerous in the surgical arts, any one of which can be employed herein.

FIG. 21 is a view of surgical instrument 160 along line 21-21. Elongated shaft 162 may be surrounded by an insulating material 176. Channel 165 of elongated shaft 162 may have wire member 174 running therethrough, cable 79 of a module 70 running therethrough, and any other leads needed to operate the jaw members 166,167.

As shown in FIGS. 22A and 22B, surgical instrument 160 includes module 70 mounted within the distal end 163 of elongated shaft 162. Module 70 may scan the anatomy within and beyond jaw members 166,167 when the members 166, 167 are in the open position as shown in FIG. 22A. Module 70 may scan the portion of the anatomy within jaw members 166,167 when in a closed position as shown in FIG. 22B. Jaw members 166,167 may be straight or arcuate over at least a portion of the jaw member. Jaw members 166,167 may include grasping or cutting elements 177,178. Grasping or cutting elements 177,178 are positioned on jaw members 166,167 in an opposed facing relationship. The surgical instrument 160 may be called a grasper when the jaw members 166,167 include grasping elements 177,178. The surgical instrument 160 may be called scissors when the jaw members 166,167 include cutting elements 177,178. The surgical instrument may be a biopsy device (i.e., biopsy forceps) that has a module 70 mounted similarly, such that the tissue to be biopsied may be scanned by module 70 before being biopsied. The module 70 may be able to emit a beam of radiation that can act to cut out the tissue or part of the anatomy to be biopsied.

In another embodiment, module 70 may be mounted onto elongated shaft 162 near distal end 163. The scanning module may be mounted on shaft 162 by being built into the body of the shaft, by being fitted into a covering that is fitted onto elongated shaft 162, or by fastening a deployable module 70 including a first fastener 82 and optionally a second fastener 84 (as shown in FIG. 9) onto elongated shaft 162.

In another embodiment, disclosed herein is a method of cutting tissue comprising the steps of grasping tissue with surgical instrument 160 including at least two jaw members 166,167 and module 70, compressing the tissue between the jaw members 166,167, and cutting the compressed tissue. The cutting step may include cutting the tissue with an ultrasonic blade, a beam of radiation from the module, or other cutting tool. The method may also include the step of scanning the anatomy with a beam of radiation from module 70. In another embodiment, the method may include the step of collecting radiation returned from the anatomy and generating a displayable image of the anatomy. The displayable image may be used to view: the tissue to be grasped before grasping, the tissue during the grasping step, the tissue compressed between the grasping arms, the tissue during the cutting step, the cut tissue after the cutting step is completed.

In the above description and drawings certain embodiments were disclosed, however, it will be apparent that variations and modifications of the embodiments may be made without departing from the principles disclosed herein or the scope of the appended claims. Accordingly, other embodiments are within the scope of the following claims.

What is claimed is:

1. A medical instrument for scanning the anatomy with a beam of radiation, the medical instrument comprising:
   a medical instrument portion that is insertable into a portion of the anatomy; and
   a module, the module comprising:
      a housing suitable for insertion in the anatomy that includes a window and a fastener to attach the housing to the medical instrument portion such that the module is carried along with the insertable portion of the medical instrument;
      an oscillating reflector within the housing that directs a beam of radiation onto the anatomy; and
      a radiation collector to receive radiation returned from the anatomy including a detector or collecting fibers connectable to a detector;
   wherein the fastener is a linkage having a distal end and a proximal end, wherein the distal end of the linkage is attached to the module and the proximal end is pivotally attached to the medical instrument portion;
   wherein the linkage comprises first linking members and second linking members disposed on each side of the medical instrument, the first linking members including a shape memory alloy actuator capable of applying a lifting force to move the module by pivoting the linkage about its proximal end.

2. The module of claim 1 wherein in an insertable configuration, the medical instrument includes a longitudinal axis and the module extends from the distal end of the insertable portion of the medical instrument along the longitudinal axis.

3. The module of claim 2 wherein the module is pivotally attached to the distal end of the linkage such that the module can be positioned in a plurality of positions to scan the anatomy.

4. The module of claim 1 wherein the second linking members include a spring elastically opposing the actuator-applied lifting force such that movement of the module is reversible upon removal of the lifting force.

5. The module of claim 4 wherein the shape memory alloy actuator contracts in response to a DC current applied to the shape memory alloy of the actuator.

6. The module of claim 1 wherein the medical instrument is an endoscope.

7. A medical instrument for use with a scanning beam device, the medical instrument comprising:
   a medical instrument shaft that is insertable in the anatomy having a distal penetrating tip, a distal end and a proximal end, and a passageway therethrough extending from the proximal end to the distal end; and a module positioned within the distal end of the medical instrument shaft to scan the anatomy and deployable into the anatomy through the passageway, the passageway being configured to receive the module proximally from the distal penetrating tip, the module comprising:
  an oscillating reflector that directs a beam of radiation on the anatomy in a bi-resonant or bi-sinusoidal scan pattern; and
  a radiation collector to receive radiation returned from the anatomy including a detector or collecting fibers connectable to a detector; and
a cable extending through the passageway from the module to a scanning beam device, the cable including a counterweight attached to the cable for applying tension to the module after the module has been deployed.

8. A surgical instrument for use with a scanning beam device, the surgical instrument comprising:
  an elongate surgical instrument shaft having a distal end, a proximal end, and a channel therethrough, the shaft including a module for scanning the anatomy positioned in the distal end thereof, the module comprising;
    a resonant reflector that directs a beam of radiation on the anatomy in a bi-resonant or bi-sinusoidal scan pattern; and
    a radiation collector to receive radiation returned from the anatomy including a detector or collecting fibers connectable to a detector;
  a plurality of jaw members pivotally disposed on the distal end of the shaft such that the jaw members pivot about a fixed point that is fixed to the distal end of the shaft, the jaw members including grasping or cutting elements positioned in an opposed facing relationship; and
  a handle at the proximal end of the shaft operatively configured to open and close the jaw members;
  wherein the resonant reflector is disposed between the jaw members and distally from a pivot axis of at least one of the plurality of jaw members, and positioned to scan between the jaw members whether open or closed.

9. A surgical stapler comprising:
  a handle portion operably configured to produce a firing motion;
  a shaft attached to the handle portion for transferring the firing motion for deploying a staple, the shaft having a proximal end and a distal end and a working channel therein;
  the shaft including a module for scanning the anatomy, the module being positioned within the working channel at the distal end of the shaft, the module comprising;
    a resonant reflector that directs a beam of radiation on the anatomy in a bi-resonant or bi-sinusoidal scan pattern; and
    a radiation collector to receive radiation returned from the anatomy including a detector or collecting fibers connectable to a detector;
  a surgical stapler end effector distally attached to the shaft, the end effector including a plurality of surgical staples which are deployed in response to the firing motion; and
  a firing mechanism responsive to the firing motion that transfers the firing motion to the end effector;
  wherein the resonant reflector is positioned to scan the portion of the anatomy that is receivable in the end effector.

* * * * *